United States Patent
Ostraat et al.

(10) Patent No.: US 11,369,950 B2
(45) Date of Patent: Jun. 28, 2022

(54) MULTI-FUNCTIONAL COMPOSITE CATALYST MATERIALS AND METHODS OF SYNTHESIZING THE CATALYST MATERIALS

(71) Applicant: Saudi Arabian Oil Company, Dhahran (SA)

(72) Inventors: Michele Ostraat, Sommerville, MA (US); Brian Hanna, West Roxbury, MA (US); Maxim Bukhovko, Boston, MA (US); Timothy J. Kucharski, Belmont, MA (US); Ke Zhang, Stoneham, MA (US); Sergio Fernandez, Somerville, MA (US)

(73) Assignee: Saudi Arabian Oil Company, Dhahran (SA)

( * ) Notice: Subject to any disclaimer, the term of this patent is extended or adjusted under 35 U.S.C. 154(b) by 817 days.

(21) Appl. No.: 15/901,442

(22) Filed: Feb. 21, 2018

(65) Prior Publication Data
US 2019/0255519 A1   Aug. 22, 2019

(51) Int. Cl.
*B01J 35/00* (2006.01)
*B01J 21/04* (2006.01)
(Continued)

(52) U.S. Cl.
CPC .......... *B01J 35/0006* (2013.01); *B01J 21/04* (2013.01); *B01J 21/063* (2013.01); *B01J 21/08* (2013.01);
(Continued)

(58) Field of Classification Search
CPC ...... B01J 35/0006; B01J 29/48; B01J 29/405; B01J 35/1014; B01J 29/076;
(Continued)

(56) References Cited

U.S. PATENT DOCUMENTS

| 3,645,684 | A |   | 2/1972  | De Cuir |
| 3,702,886 | A | * | 11/1972 | Argauner ................ C01B 39/40 |
|           |   |   |         | 423/705 |

(Continued)

FOREIGN PATENT DOCUMENTS

| EP | 276096 A1    | 7/1988 |
| WO | 2005016823 A1 | 2/2005 |

(Continued)

OTHER PUBLICATIONS

U.S. Office Action dated Aug. 12, 2020 pertaining to U.S. Appl. No. 16/256,641, filed Jan. 24, 2019, 26 pgs.

(Continued)

*Primary Examiner* — Anthony J Zimmer
(74) *Attorney, Agent, or Firm* — Dinsmore & Shohl LLP

(57) ABSTRACT

A multi-functional composite catalyst includes a catalyst support material, a preformed catalyst material at least partially secured in the catalyst support, and at least one catalytically active compound supported by the catalyst support, the preformed catalyst material, or both. The catalyst support material may include fumed silica, alumina, fumed alumina, fumed titania, or combinations of these. A catalytic activity of the catalytically active compound may be different than a catalytic activity of the preformed catalyst material. The composite catalyst may be catalyst for producing propene from 2-butene and may include a zeolite as the preformed catalyst material and a metal oxide, such as tungsten oxide, as the catalytically active material. A method of making the composite catalyst may include aerosolizing a catalyst precursor mixture that includes a preformed catalyst material, catalyst support precursor, and catalytically active compound precursor, and drying the aerosolized catalyst precursor mixture.

26 Claims, 11 Drawing Sheets

(51) Int. Cl.
| | |
|---|---|
| *B01J 21/06* | (2006.01) |
| *B01J 21/08* | (2006.01) |
| *B01J 23/02* | (2006.01) |
| *B01J 23/10* | (2006.01) |
| *B01J 23/28* | (2006.01) |
| *B01J 23/30* | (2006.01) |
| *B01J 23/34* | (2006.01) |
| *B01J 23/36* | (2006.01) |
| *B01J 29/40* | (2006.01) |
| *B01J 29/78* | (2006.01) |
| *B01J 35/02* | (2006.01) |
| *B01J 35/10* | (2006.01) |
| *B01J 37/00* | (2006.01) |
| *B01J 37/02* | (2006.01) |
| *B01J 29/48* | (2006.01) |
| *C07C 6/04* | (2006.01) |
| *B01J 29/076* | (2006.01) |
| *B01J 29/06* | (2006.01) |

(52) U.S. Cl.
CPC ............. *B01J 23/02* (2013.01); *B01J 23/10* (2013.01); *B01J 23/28* (2013.01); *B01J 23/30* (2013.01); *B01J 23/34* (2013.01); *B01J 23/36* (2013.01); *B01J 29/061* (2013.01); *B01J 29/076* (2013.01); *B01J 29/40* (2013.01); *B01J 29/405* (2013.01); *B01J 29/48* (2013.01); *B01J 29/783* (2013.01); *B01J 35/023* (2013.01); *B01J 35/1014* (2013.01); *B01J 35/1019* (2013.01); *B01J 35/1023* (2013.01); *B01J 35/1042* (2013.01); *B01J 37/0045* (2013.01); *B01J 37/0054* (2013.01); *B01J 37/0207* (2013.01); *C07C 6/04* (2013.01); *B01J 2229/12* (2013.01); *B01J 2229/186* (2013.01); *B01J 2229/20* (2013.01); *B01J 2229/42* (2013.01)

(58) Field of Classification Search
CPC .. B01J 35/1042; B01J 29/061; B01J 37/0045; B01J 21/04; B01J 21/063; B01J 21/08; B01J 23/02; B01J 23/10; B01J 23/28; B01J 23/30; B01J 23/34; B01J 23/36; B01J 29/40; B01J 29/783; B01J 35/023; B01J 35/1019; B01J 35/1023; B01J 37/0054; B01J 37/0207; B01J 2229/186; B01J 2229/42; B01J 2229/12; B01J 2229/20; C07C 6/04; Y02P 20/52
See application file for complete search history.

(56) References Cited

U.S. PATENT DOCUMENTS

| | | |
|---|---|---|
| 3,865,751 A | 2/1975 | Banks et al. |
| 3,928,177 A | 12/1975 | Hayes |
| 4,507,396 A * | 3/1985 | Hickson ............... B01J 2/00 502/60 |
| 4,575,575 A | 3/1986 | Drake et al. |
| 4,684,760 A | 8/1987 | Drake |
| 4,967,013 A * | 10/1990 | Steck ............... C07C 45/673 568/433 |
| 5,204,088 A | 4/1993 | Noebel et al. |
| 5,230,789 A | 7/1993 | Chao et al. |
| 5,304,692 A | 4/1994 | Yamada et al. |
| 5,340,560 A | 8/1994 | Rohr et al. |
| 6,099,719 A * | 8/2000 | Cody ............... C10G 65/04 208/57 |
| 6,551,567 B2 | 4/2003 | Konya et al. |
| 6,586,785 B2 | 7/2003 | Flagan et al. |
| 6,723,606 B2 | 4/2004 | Flagan et al. |
| 6,780,805 B2 | 8/2004 | Faber et al. |
| 8,097,555 B2 | 1/2012 | Costa et al. |
| 8,246,933 B2 | 8/2012 | Jiang et al. |
| 8,415,267 B2 | 4/2013 | Lee |
| 8,440,874 B2 | 5/2013 | Ramachandran et al. |
| 8,895,795 B2 | 11/2014 | Krawczyk et al. |
| 9,586,198 B2 | 3/2017 | Park et al. |
| 9,682,367 B2 | 6/2017 | Ali et al. |
| 9,969,621 B2 | 5/2018 | Ostraat |
| 2002/0035950 A1 | 3/2002 | Mangold et al. |
| 2002/0177311 A1 | 11/2002 | Schumacher et al. |
| 2004/0101454 A1 | 5/2004 | Johnson et al. |
| 2005/0118096 A1 | 6/2005 | Robson et al. |
| 2008/0011876 A1 | 1/2008 | Ostraat |
| 2010/0056839 A1 | 3/2010 | Ramachandran et al. |
| 2010/0286432 A1 | 11/2010 | Tateno et al. |
| 2010/0286458 A1 | 11/2010 | Iselborn et al. |
| 2011/0077444 A1 | 3/2011 | Butler |
| 2011/0092757 A1 | 4/2011 | Akagishi et al. |
| 2011/0196184 A1 | 8/2011 | Popp et al. |
| 2011/0306691 A1 * | 12/2011 | Sosa ............... B29C 44/08 521/79 |
| 2012/0016172 A1 | 1/2012 | Miyazoe et al. |
| 2012/0039782 A1 | 2/2012 | Nicholas |
| 2014/0027346 A1 | 1/2014 | Chaumonnot et al. |
| 2014/0124410 A1 * | 5/2014 | Rayo Mayoral ....... B01J 29/045 208/111.3 |
| 2017/0001925 A1 | 1/2017 | Abudawoud et al. |
| 2017/0136445 A1 | 5/2017 | Ostraat et al. |
| 2017/0320747 A1 | 11/2017 | Ostraat |

FOREIGN PATENT DOCUMENTS

| | | |
|---|---|---|
| WO | 2016061262 A1 | 4/2016 |
| WO | 2016068814 A1 | 5/2016 |
| WO | 2017083162 A1 | 5/2017 |
| WO | 2018136576 A1 | 7/2018 |

OTHER PUBLICATIONS

Notice of Allowance and Fee(s) Due dated Feb. 16, 2021 pertaining to U.S. Appl. No. 16/256,641, filed Jan. 24, 2019, 11 pgs.

Bhuiyan et al., "Kinetics Modelling of 2-Butene Metathesis over Tungsten Oxide Containing Mesoporous Silica Catalyst", The Canadian Journal of Chemical Engineering, 2014, 92, 1271-1282, Canadian Society for Chemical Engineering.

Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 467, 224-234, Elsevier.

Bukhovko et al., "Continuous Aerosol Flow Reactors for the Controlled Synthesis of heterogeneous Catalyst Particles", AIChE Annual Meeting, Nov. 8-13, 2015.

Debecker et al., "A Non-Hydrolytic Sol-Gel Route to Highly Active MoO2-SiO2-Al2O3 metathesis Catalysts", Catalysis Science & Technology, 2012, 2:6, 1075-1294, RSC Publishing.

Debecker et al., "Aerosol Route to Nanostructured WO3-SiO2-Al2O3 Metathesis Catalysts: Toward Higher Propene Yield", Applied Catalysis A: General, 2014, 470, 458-466, Elsevier.

Debecker et al., "Flame-Made MoO3/SiO2-Al2o3 Metathesis Catalysts with highly Dispersed and Highly Active Molybdate Species", Journal of Catalysis, 2011, 277, 154-163, Elsevier.

Hyeon-Lee et al., "Fractal Analysis of Flame-Synthesized Nanostructured Silica and Titania Powders Using Small-Angle X-Ray Scattering", Langmuir 1998, 5751-5756, 14, American Chemical Society.

International Search Report and Written Opinion for serial No. PCT/US2017/030014, dated Jul. 11, 2017.

International Search Report and Written Opinion pertaining to PCT/US2016/060258 dated Mar. 7, 2017.

Ishihara et al., "Hydrocracking of 1-methylnaphthalene/decahydronaphthalene mixture catalyzed by zeolite-alumina composite supported NiMo catalysts", Fuel Processing Technology 116, pp. 222-227, 2013.

Keskinen et al., "On-Line Characterization of Morphology and Water Adsorption on Fumed Silica Nanoparticles", Aerosol Science

(56) References Cited

OTHER PUBLICATIONS and Technology, 2011, 1441-1447, 45, American Association for Aerosol Research.

Lin et al., "Aerosol Processing of Low-Cost Mesoporous Silica Spherical Particles from Photonic Industrial Waste Powder for C02 Capture", Chemical Engineering Journal, 2012, 215-222, 197, Elsevier B.V.

Liu et al., "Alumina with Various pore Structures Prepared by Spray Pyrolysis of Inorganic Aluminum Precursors", I&EC Research, 2013, 52, 13377-13383, ACS Publications.

Lu et al., "Aersol-Assisted Self-Assembly of Mesostructured Spherical Nanoparticles", Nature, 1999, vol. 398, Macmillan Magazines Ltd.

Maksasithorn, Surasa et al., "Preparation of super-microporous WO3-SiO2 olefin metathesis catalysts by the aerosol-assisted sol-gel process", pp. 125-133, Microporous and Mesoporous Materials 213 (2015).

Notice of Allowance pertaining to U.S. Appl. No. 15/146,037, filed May 4, 2016, 8 pages.

Non-Final Office Action dated Sep. 25, 2017 pertaining to U.S. Appl. No. 15/252,733, filed Aug. 31, 2016.

Xie et al., "An Overview of Recent Development in Composite Catalysts from Porous Materials for Various Reactions and Processes", Int. J. Mol. Sci. 11, pp. 2152-2187, 2010.

Notice of Allowance pertaining to U.S. Appl. No. 15/252,733, filed Aug. 31, 2016, 8 pages.

Popoff et al., "Expanding the scope of metathesis: a survey of polyfunctional, single-site supported tungsten systems for hydrocarbon valorization", Chemical Society Reviews, Issue 23 (2013).

Mazoyer, et al., "Production of propylene from 1-butene on highly active "Bi-functional single active site" catalyst Tungsten carbene-hydride supported on alumina" http://dialog-proqquest.com/professional/printviewfile?accountid=157282 Accessed: Jul. 6, 2017.

Office Action dated Jan. 24, 2020 pertaining to U.S. Appl. No. 16/256,641, filed Jan. 24, 2019, 7 pgs.

Office Action pertaining to U.S. Appl. No. 15/949,726, dated Jun. 7, 2018.

International Search Report and Written Opinion dated Dec. 3, 2018 pertaining to International Application No. PCT/US2018/046696 filed Aug. 14, 2018.

Silverman et al., Methods of Generating Solid Aerosels, J Air Pollution Control Assoc., 6:2 (1956), 76-83.

Garcia et al. Multifaceted tungsten oxide films grown by thermal evaporation, Surf Coat Tech, 283 (2015) 177-183.

Office Action dated Oct. 3, 2019 pertaining to U.S. Appl. No. 15/998,699, filed Aug. 16, 2018, 32 pgs.

International Search Report and Written Opinion dated May 24, 2019 pertaining to International application No. PCT/US2019/018541 filed Feb. 19, 2019, 17 pgs.

Office Action dated Apr. 1, 2020 pertaining to U.S. Appl. No. 15/998,699, filed Aug. 16, 2018, 16 pgs.

International Search Report and Written Opinion dated Apr. 9, 2020 pertaining to International application No. PCT/US2020/012309 filed Jan. 6, 2020, 12 pgs.

U.S. Office Action dated Jul. 9, 2021 pertaining to U.S. Appl. No. 16/909,083, filed Jun. 23, 2020, 35 pages.

Spamer, A. et al ("The Reduction of Isomerization Activity on a WO3/SiO2 Metathesis Catalyst," Appl Cata A: General 255 (2003) 153-167) (Year: 2003).

European Office Action pertaining to application No. 18772960.3 dated May 26, 2021.

U.S. Office Action dated Jan. 10, 2022 pertaining to U.S. Appl. No. 16/909,083, filed Jun. 23, 2020, 26 pages.

Chauvin, J. et al., "Comparative Influence of Surface Tungstate Species and Bulk Amorphous WO3 Particles on the Acidity and Catalytic Activity of Tungsten Oxide Supported on Silica", J. Phys. Chem. C., 2015, 119, pp., 12345-12355.

U.S. Notice of Allowance and Fee(s) Due dated Feb. 4, 2022 pertaining to U.S. Appl. No. 17/318,256 filed May 12, 2021, 32 pages.

\* cited by examiner

MULTI-FUNCTIONAL COMPOSITE CATALYST MATERIALS AND METHODS OF SYNTHESIZING THE CATALYST MATERIALS

TECHNICAL FIELD

Embodiments of the present disclosure generally relate to catalytic materials and methods of synthesizing catalytic materials.

BACKGROUND

In recent years, there has been a dramatic increase in the demand for propene to feed the growing markets for polypropylene, propylene oxide, and acrylic acid. Currently, most of the propene produced worldwide (74 million tons/year) is a by-product from steam cracking units (57%), which primarily produce ethylene, or a by-product from Fluid Catalytic Cracking (FCC) units (30%), which primarily produce gasoline. These processes cannot respond adequately to a rapid increase in propene demand.

Raffinate is the residue C4 stream from a naphtha cracking process or from a gas cracking process when components are removed (the C4 stream typically containing, as its chief components, n-butane, 1-butene, 2-butene, isobutene, and 1,3-butadiene, and optionally some isobutane and said chief components together forming up to 99% or more of the C4 stream). Specifically, Raffinate-2 is the C4 residual obtained after separation of 1,3-butadiene and isobutene from the C4 raffinate stream and consists mainly of cis- or trans-2-butene, 1-butene, and n-butane. Similarly, Raffinate-3 is the C4 residual obtained after separation of 1,3-butadiene, isobutene, and 1-butene from the C4 raffinate stream and consists mainly of cis- or trans-2-butene, n-butane, and unseparated 1-butene. Utilizing Raffinate-2 and Raffinate-3 streams for conversion to propene is desirable to increase the available supply of propene.

Production of propene from a butene containing stream can be accomplished through metathesis of the butene to propene and other compounds in combination with cracking, isomerization or both. Some propene processes include metathesis, isomerization, and cracking in order to increase the overall yield and propene selectivity of the reaction system. Each of these types of reactions requires a different catalyst, such as a cracking catalyst for the cracking reaction, a metathesis catalyst for the metathesis reaction, and an isomerization catalyst to conduct the isomerization. In conventional reaction system for converting butene to propene, the separate catalysts may be isolated in separate catalyst zones, such as by charging each of the separate catalysts to a separate reactor or by charging the catalyst to a single reactor and separating each catalyst with inert spacers, such as quartz wool. Segregating the catalysts into separate reactor vessels substantially increases the initial capital cost of the reaction system. Additionally, separating the catalysts with inert spacers creates dead volumes in the reactor, which may reduce the efficiency of the reactor.

To reduce costs and eliminate dead zones, a physical catalyst mixture of two or more separate solid particulate catalyst materials may be used. However, these physical catalyst mixtures of different solid catalyst materials may gradually segregate in the reactor over time due to settling that occurs with continuing use and handling. Thus, the effectiveness of the physical catalyst mixtures of solid catalyst particles may decrease over time as the separate catalysts segregate through settling.

SUMMARY

Accordingly, there is an ongoing need for multi-functional composite catalysts and methods of synthesizing multi-functional composite catalysts. Embodiments of the present disclosure are directed to multi-functional composite catalysts that include a plurality of catalyst particles, each of the catalyst particles including a plurality of different catalytically active species. Each of the plurality of catalytically active species in the composite catalyst provides a different catalytic functionality to the catalyst particles. Thus, the multi-functional composite catalyst combines multiple catalytic functionalities into a single particle. The multi-functional composite catalyst may enable a single particulate catalyst to be charged to a reactor to conduct a plurality of different chemical reactions, such as combinations of isomerization, metathesis, and cracking for producing propene from 2-butene, for example.

According to some embodiments, composite catalyst may include a catalyst support material that includes at least one of fumed silica, alumina, fumed alumina, fumed titania, or combinations of these, a preformed catalyst material at least partially secured in the catalyst support, and at least one catalytically active compound supported by the catalyst support, the preformed catalyst material, or both. A catalytic activity of at least one catalytically active compound may be different than a catalytic activity of the preformed catalyst material.

According to other embodiments, a method of producing a composite catalyst may include generating an aerosolized catalyst precursor mixture by aerosolizing a catalyst precursor mixture comprising a preformed catalyst material, a catalyst support precursor, at least one catalytically active compound precursor, and a diluent. The preformed catalyst material is a particulate solid and the catalyst support precursor comprises at least one of fumed silica, a soluble aluminum salt, fumed alumina, fumed titania, or combinations of these. The method may further include drying the aerosolized catalyst precursor mixture to produce a plurality of composite catalyst particles. Drying may cause the catalyst support precursor to form an open porous structure of catalyst support material encasing the preformed catalyst material. The catalytically active compound may be distributed throughout the catalyst support material.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
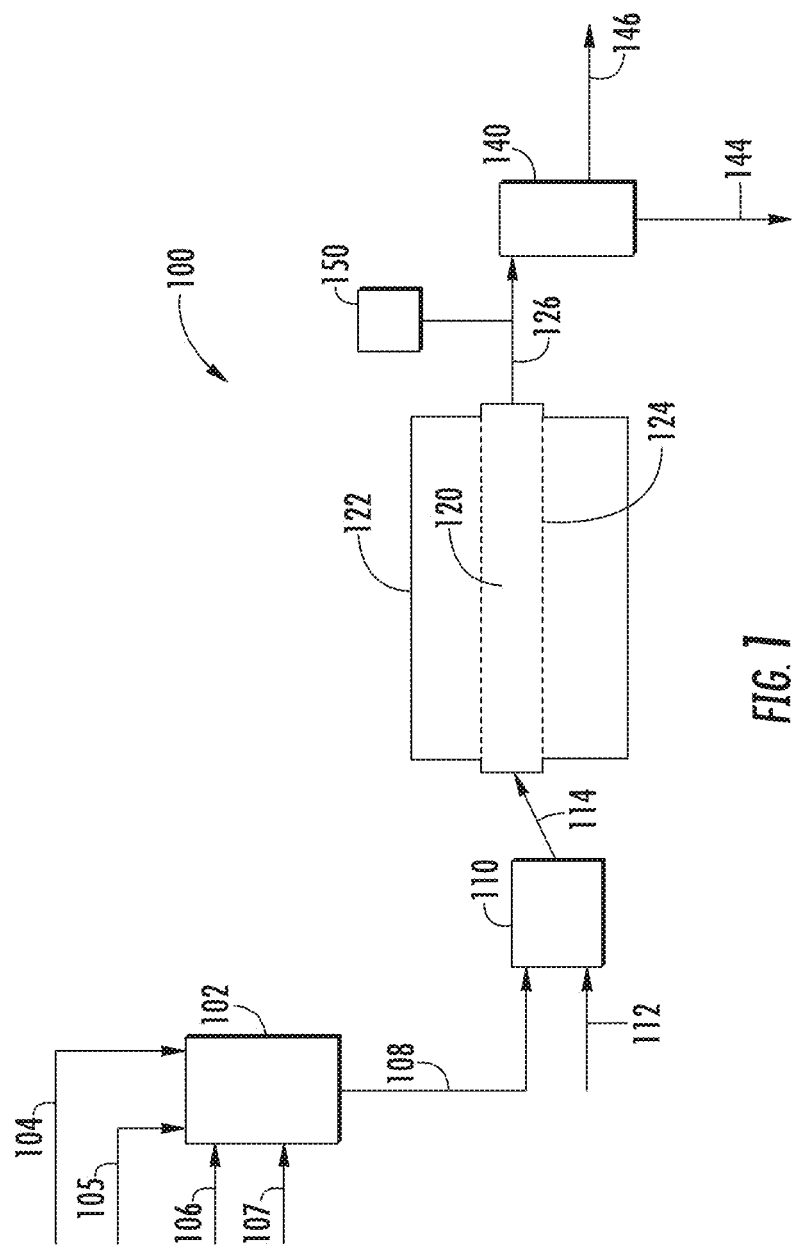
FIG. 1 schematically depicts an aerosol processing system, in accordance with one or more embodiments of the present disclosure.
Figure 3:
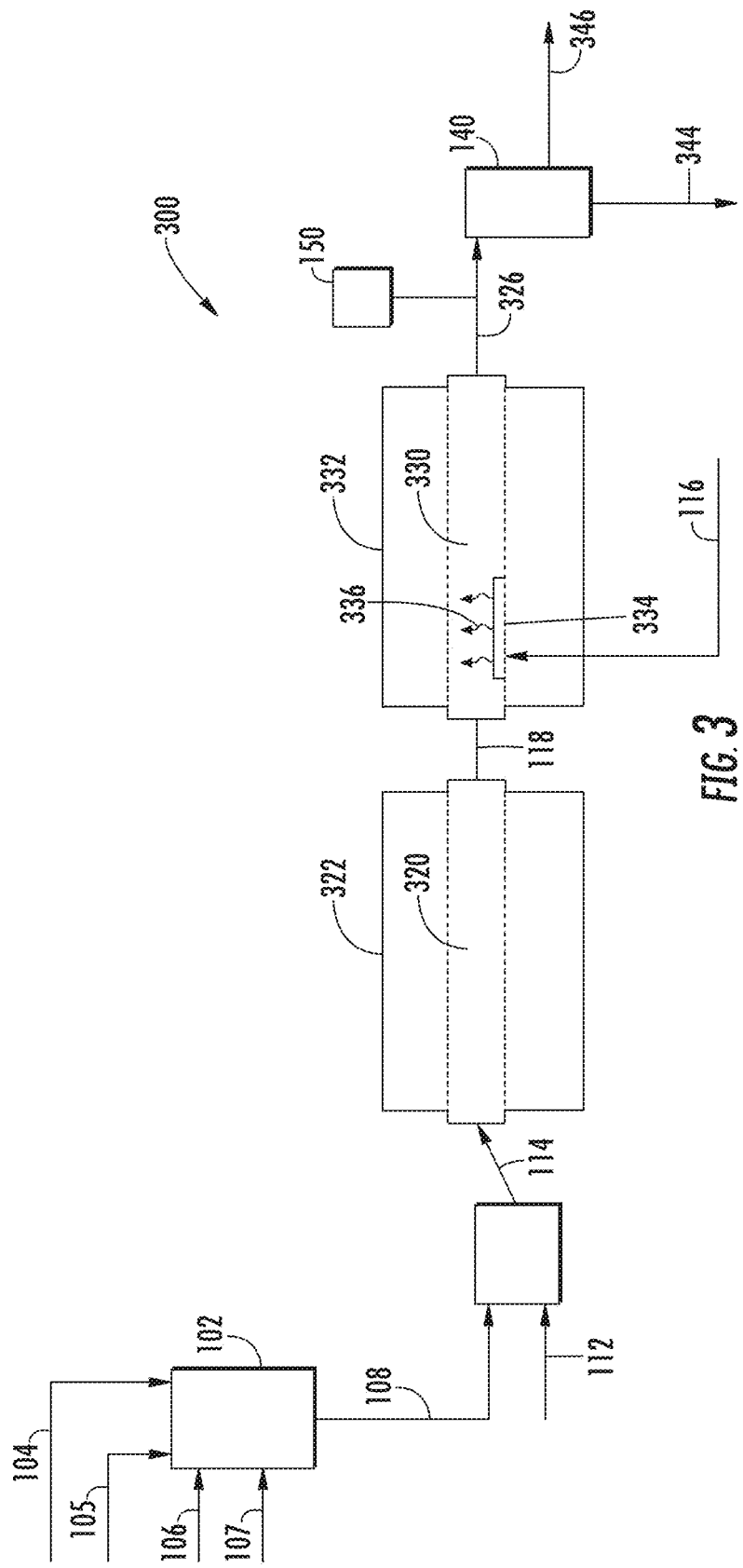
FIG. 3 schematically depicts another aerosol processing system, in accordance with one or more embodiments of the present disclosure.
Figure 4:
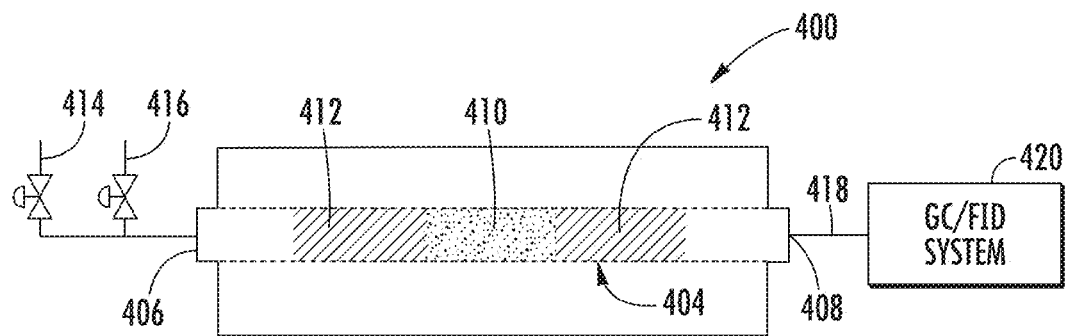
FIG. 4 schematically depicts a reaction system for converting 2-butene to propene using the multi-functional composite catalyst, in accordance with one or more embodiments of the present disclosure.

For the purpose of describing the simplified schematic illustrations and descriptions of FIGS. 1, 3, and 4, the numerous valves, temperature sensors, electronic controllers, and the like that may be employed and well known to those of ordinary skill in the art of certain chemical processing operations are not included. Further, accompanying components that are often included in typical chemical processing operations, carrier gas supply systems, pumps, compressors, furnaces, or other subsystems are not depicted. It should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system or a system inlet stream which enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1, 3, and 4. Mixing or combining may also include mixing by directly introducing both streams into a like system component, such as a vessel, aerosolizer, heating zone, furnace, or other system component. For example, it should be understood that when two streams are depicted as being combined directly prior to entering a system component, the streams could equivalently be introduced into the system component and be mixed in the system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to multi-functional composite catalysts and methods of synthesizing the composite catalysts via aerosol processing. In some embodiments, the composite catalyst may include a catalyst support material including at least one of fumed silica, alumina, fumed alumina, fumed titania, or combinations of these. The composite catalyst may also include a preformed catalyst material at least partially secured in the catalyst support and at least one catalytically active compound supported by the catalyst support, the preformed catalyst material, or both. A catalytic activity of at least one catalytically active compound is different than a catalytic activity of the preformed catalyst material. In other embodiments, an aerosol processing method of forming the composite catalysts is disclosed. The method includes generating an aerosolized catalyst precursor mixture by aerosolizing a catalyst precursor mixture comprising a preformed catalyst material, a catalyst support precursor, at least one catalytically active compound precursor, and a diluent. The preformed catalyst material may be a particulate solid, and the catalyst support precursor may include at least one of fumed silica, a soluble aluminum salt, fumed alumina, fumed titania, or combinations of these. The method may further include drying the aerosolized catalyst precursor mixture to produce a plurality of composite catalyst particles. Drying may cause the catalyst support precursor to form an open porous structure of catalyst support material encasing the preformed catalyst material. The catalytically active compound may be distributed throughout the catalyst support material.

The composite catalyst provides a multi-functional catalyst having at least two distinct catalytic species, each catalytic species capable of catalyzing a different reaction independent of the other catalytic species in the composite catalyst. For example, in some embodiments, the composite catalyst may be useful for converting 2-butene to propene and may include a zeolite as the single catalyst material and a tungsten oxide as the catalytically active material. The tungsten oxide may be one of the two distinct catalytic species and may be included to cross-metathesize 1-butene and 2-butene to produce propene, pentene, and optionally other $C_{6+}$ olefins. The zeolite may be the other distinct catalytic species and may be included to catalytically crack the pentene or other larger olefins into propene and other smaller olefins.

The composite catalyst may enable a reaction system to perform multiple catalytic reactions without requiring handling and management of multiple catalyst materials. Further, use of the composite catalyst may eliminate the need to install spacer materials in a reactor to separate catalyst beds having different catalysts. This may eliminate dead zones from a reactor. Dead zones are zones in which no reaction takes place, such as due to the presence of spacing materials. In some conventional reaction systems, a blend of two separate particulate catalysts may be prepared and charged to the reactor. Although a blend of two particulate catalysts may initially provide a multi-functional catalytic environment within a reactor system, one of the particulate catalysts may eventually settle to the bottom of the reactor under the force of gravity, which may create a separation of the two blended catalysts into separate zones in the reactor. The composite catalyst described in this disclosure eliminates the problems associated with a blended catalyst settling out in a reaction system over time.

As used in this disclosure, a "catalyst" refers to a solid particulate comprising catalyst support material and at least one catalytically active compound.

As used in this disclosure, a "catalytically active compound" refers to any substance which increases the rate of a specific chemical reaction. Catalytically active compounds and the catalysts made with the catalytically active compounds described in this disclosure may be utilized to promote various reactions, such as, but not limited to, isomerization, metathesis, cracking, hydrogenation, demetalization, desulfurization, denitrogenation, other reactions, or combinations of these.

As used in this disclosure, "catalytic activity" refers to a degree to which the catalyst increases the reaction rate of a reaction. Greater catalytic activity of a catalyst increases the reaction rate of a reaction compared to a catalyst having a lesser catalytic activity.

As used in this disclosure, "preformed catalyst material" may include a catalyst material with catalytic activity that has previously been synthesized into a solid catalyst particle having a plurality of catalytically active sites. Preformed catalyst materials are generally capable of being utilized as solid particulate catalysts prior to incorporating the material into the composite catalyst. For example, preformed catalyst materials may include zeolites.

As used in this disclosure, the term "dopant" refers to a constituent of the composite catalyst comprising less than 2% by weight of the composite catalyst.

As described in this disclosure, according to one or more embodiments, the multi-functional composite catalyst may include a preformed catalyst material. The preformed catalyst material may be a solid particulate catalyst exhibiting catalytic activity without further processing of the preformed catalyst material. The preformed catalyst material may be a particulate solid. Examples of preformed catalyst materials may include zeolites, alkaline-metal oxides such as magnesium oxide or calcium oxide, transition metal oxides or sulfides, or other metal- or metal-oxide-based catalysts.

In some embodiments, the preformed catalyst material may include one or more than one zeolite compositions. As used in this disclosure, a zeolite composition refers to a zeolite with a particular zeolitic framework structure and having a particular material composition. Thus, zeolite compositions may differ between one another by framework structure, composition, or both. Zeolite compositions may be grouped into "zeolite types" such as MFI framework type zeolites (such as ZSM-5 zeolite), FAU framework type zeolites (such as Y zeolite), or *BEA framework type zeolites (such as zeolite Beta), each of which is described subsequently in this disclosure. Other zeolite types having other framework types and compositions may also be used to produce the composite catalyst.

In one or more embodiments, the preformed catalyst material may comprise one or more MFI framework type zeolites, such as ZSM-5. As used in this disclosure, "ZSM-5" refers to zeolites having an MFI framework type according to the IUPAC zeolite nomenclature and consisting of silica and alumina. ZSM-5 refers to "Zeolite Socony Mobil-5" and is a pentasil family zeolite that can be represented by the chemical formula $Na_nAl_nSi_{96-n}O_{192}\cdot 16H_2O$, where $0<n<27$. Examples of commercially available zeolite ZSM-5 include CBV2314, CBV3024E, CBV5524G and CBV28014 (available from Zeolyst International). According to one or more embodiments, the MFI framework type zeolite may comprise one or more phosphorous-containing compounds, such as a phosphorous oxide, such as phosphorous pentoxide ("$P_2O_5$").

In one or more embodiments, the catalyst composition may comprise a FAU framework type zeolite, such as zeolite Y. As used in this disclosure, "zeolite Y" refers to zeolite having a FAU framework type according to the IUPAC zeolite nomenclature and consisting of silica and alumina, where the molar ratio of silica to alumina is at least 3. For example, the molar ratio of silica to alumina in the zeolite Y may be at least 5, at least 12, or even at least 30, such as from 5 to 30, from 12 to 30, or from about 15 to about 30. The unit cell size of the zeolite Y may be from about 24 Angstrom to about 25 Angstrom, such as 24.56 Angstrom.

In one or more embodiments, the catalyst composition may comprise one or more *BEA framework type zeolites, such as zeolite Beta. As used in this disclosure, "zeolite Beta" refers to zeolite having a *BEA framework type according to the IUPAC zeolite nomenclature and consisting of silica and alumina. The molar ratio of silica to alumina in the zeolite Beta may be at least 10, at least 25, or even at least 100. For example, the molar ratio of silica to alumina in the zeolite Beta may be from 5 to 500, such as from 25 to 300. Examples of commercially available zeolite Beta compositions may include, but are not limited to, CP814C, CP814E and CP811C-300 (produced by Zeolyst International). The zeolite Beta may be in the form of H-Beta. H-Beta refers to the acidic form of zeolite Beta usually derived from ammonium-Beta ($NH_4$-Beta) via calcination. In one or more embodiments, the zeolite Beta may be stabilized by direct reaction with phosphoric acid ($H_3PO_4$) or by impregnation with ammonium hydrogen phosphate (($NH_4$)$_2$$HPO_4$). According to one or more embodiments, the *BEA framework type zeolite may comprise one or more phosphorous-containing compounds, such as a phosphorous oxide or phosphorous pentoxide ("$P_2O_5$").

The zeolite incorporated into the composite catalyst as the preformed catalyst material may have an alumina content great enough to provide sufficient catalytic activity to the zeolite. In some embodiments, the zeolite may have a weight ratio of silica to alumina sufficient to provide the composite catalyst with an overall silica to alumina weight ratio of 4000:1 when combined with the catalyst support material. In some embodiments, the zeolite may have a weight ratio of silica to alumina of from 10:1 to 6000:1. In other embodiments, the zeolite may have a weight ratio of silica to alumina of from 10:1 to 4000:1, from 10:1 to 2000:1, from 10:1 to 1000:1, from 10:1 to 500:1, from 10:1 to 300:1, from 100:1 to 6000:1, from 100:1 to 4000:1, from 100:1 to 2000:1, from 100:1 to 1000:1, from 100:1 to 500:1, from 200:1 to 6000:1, from 200:1 to 4000:1, from 200:1 to 2000:1, from 200:1 to 1000:1, from 200:1 to 500:1, from 500:1 to 6000:1, from 500:1 to 4000:1, from 500:1 to 2000:1, from 500:1 to 1000:1, from 1000:1 to 6000:1, from 1000:1 to 4000:1, or from 1000:1 to 2000:1, based on the total weight of the zeolite. For example, in some embodiments, the preformed catalyst material may include MFI 2000 zeolite catalyst that includes a weight ratio of silica to alumina of 2000:1. Alternatively, in other embodiments, the preformed catalyst material may include MFI-371 zeolite catalyst, which may include a weight ratio of silica to alumina of 371:1. Other zeolite materials are contemplated for the preformed catalyst material.

Preformed catalyst materials other than zeolites may also be incorporated into the composite catalyst. For example, ceria (cerium dioxide, $CeO_2$) catalyst particles, titania (titanium dioxide, $TiO_2$) catalyst particles, magnesium oxide (MgO) catalyst particles, or other preformed catalyst materials may be included in the composite catalyst.

The preformed catalyst material may have an average pore size sufficient to enable reactants to access catalytically active sites on the surfaces of the preformed catalyst material. In some embodiments, the preformed catalyst material may have an average pore size of from 0.3 nanometers (nm) to 20.0 nm, such as from 0.3 nm to 10.0 nm, from 0.3 nm to 7.0 nm, from 0.3 nm to 4.0 nm, from 0.3 nm to 2.0 nm, from 0.5 nm to 20.0 nm, from 0.5 nm to 10.0 nm, from 0.5 nm to 7.0 nm, from 0.5 nm to 4.0 nm, from 0.5 nm to 2.0 nm, from 1.0 nm to 20.0 nm, from 1.0 nm to 10.0 nm, from 1.0 nm to 7.0 nm, from 1.0 nm to 4.0 nm, from 2.0 nm to 20.0 nm, from 2.0 nm to 10.0 nm, from 2.0 nm to 7.0 nm, from 2.0 nm to 4.0 nm, from 4.0 nm to 20.0 nm, from 4.0 nm to 10.0 nm, from 4.0 nm to 7.0 nm, or from 7.0 nm to 10.0 nm. The preformed catalyst material may have an average surface area sufficient to provide the catalytically active sites on the preformed catalyst material to catalyze the reaction. In some embodiments, the preformed catalyst material may have an average surface area of from 50 square meters per gram ($m^2/g$) to 1600 $m^2/g$, such as from 50 $m^2/g$ to 1200 $m^2/g$, from 50 $m^2/g$ to 900 $m^2/g$, from 50 $m^2/g$ to 500 $m^2/g$, from 100 $m^2/g$ to 1600 $m^2/g$, from 100 $m^2/g$ to 1200 $m^2/g$, from 100 $m^2/g$ to 900 $m^2/g$, from 100 $m^2/g$ to 500 $m^2/g$, from 300 $m^2/g$ to 1600 $m^2/g$, from 300 $m^2/g$ to 1200 $m^2/g$, from 300 $m^2/g$ to 900 $m^2/g$, from 300 $m^2/g$ to 500 $m^2/g$, from 500 $m^2/g$ to 1600 $m^2/g$, from 500 $m^2/g$ to 1200 $m^2/g$, or from 500 $m^2/g$ to 900 $m^2/g$.

In some embodiment, the preformed catalyst materials may include particles having an average particle size small enough for the preformed catalyst material to be encased or secured within the catalyst support material. In some embodiments, the preformed catalyst materials may include nano-sized particulate solid particles. In some embodiments, the preformed catalyst materials may include an average particle size of from 100 nm to 2 micrometers (microns µm), such as from 100 nm to 1 µm, from 100 nm to 500 nm, from 500 nm to 2 µm, from 500 nm to 1 µm, or from 1 µm to 2 µm.

The composite catalyst may have an amount of the preformed catalyst material sufficient to improve the reaction rate of the chemical reaction catalyzed by the preformed catalyst material. In some embodiments, the composite catalyst may include from 5 wt. % to 50 wt. % preformed catalyst material, based on the total weight of the composite catalyst. In some embodiments, the composite catalyst may include from 5 wt. % to 40 wt. %, from 5 wt. % to 30 wt. %, from 5 wt. % to 20 wt. %, from 5 wt. % to 10 wt. %, from 10 wt. % to 50 wt. %, from 10 wt. % to 40 wt. %, from 10 wt. % to 30 wt. %, from 10 wt. % to 20 wt. %, from 20 wt. % to 50 wt. %, from 20 wt. % to 40 wt. %, from 20 wt. % to 30 wt. %, from 30 wt. % to 50 wt. %, from 30 wt. % to 40 wt. %, or from 40 wt. % to 50 wt. % preformed catalyst material based on the total weight of the composite catalyst.

The catalyst support may secure the preformed catalyst material within a three-dimensional support structure of the catalyst support. Additionally, the catalyst support may provide support for the catalytically active compounds. In some embodiments, the catalyst support material of the catalyst support may act as a bonding agent to bond the preformed catalyst material within the three-dimensional support structure. The catalyst support material may be stable in air and in the presence of water. The catalyst support may include fumed silica, alumina, fumed alumina, fumed silica/alumina, fumed titania, or combinations of these. The catalyst support may also include fumed ceria, mesoporous silica, or other catalyst support material or combinations of catalyst support materials. As used in the present disclosure, "mesoporous" refers to a material having an average pore size of greater than 2 nanometers and less than 50 nanometers. In some embodiments, the catalyst support may include at least one of fumed silica, alumina, fumed alumina, fumed silica/alumina, fumed titania, or combinations of these. In some embodiments, the catalyst support may include fumed silica. Alternatively, in some other embodiments, the catalyst support material may include fumed silica/alumina.

In some embodiments, the catalyst support material may include mesoporous structured silica or mesoporous structured silica/alumina materials. However, these materials may be substantially more expensive and may result in a less open and porous structure that may provide less efficient mass transfer of reactants through the catalyst support material compared to the fumed silica, alumina, fumed alumina, or fumed titania.

In some embodiments, the catalyst support material may be fumed silica/alumina and may have a weight ratio of silica to alumina sufficient, in combination with the preformed catalyst material, to provide the composite catalyst with an overall silica to alumina weight ratio of from 200:1 to 2000:1. For example, in some embodiments, the catalyst support material may have a weight ratio of silica to alumina of from 400:1 to 2000:1. In other embodiments, the catalyst support particle may have a weight ratio of silica to alumina of from 400:1 to 1600:1, from 400:1 to 1200:1, from 400:1 to 800:1, from 800:1 to 2000:1, from 800:1 to 1600:1, from 800:1 to 1200:1, from 1200:1 to 2000:1, from 1200:1 to 1600:1, or from 1600:1 to 2000:1.

Selection of fumed silica, alumina, fumed alumina, fumed silica/alumina, fumed titania, or other fumed materials for the catalyst support material may result in an increased surface area. For example, small, spherical particles of silica form branched, chain-like aggregates of fumed silica that are stable and pure. These aggregates of fumed silica have a greater boundary fractal dimension compared to other catalyst support materials. For example, the fractal dimension of fumed silica may be in a range from 1.8 to 2.0. The greater boundary fractal dimension of the fumed silica results in the aggregates of fumed silica packing or agglomerating together in loose networks, which results in the fumed silica having a reduced bulk density. The other fumed materials exhibit similar fractal dimensions that result in the aggregates of the fumed materials agglomerating together in loose networks. When aerosolized, the aggregates of the fumed materials agglomerate together to produce dried agglomerate particles. Due to the greater fractal dimension of the fumed material aggregates, agglomerate particles of the fumed material exhibit a surface area that is comparable to the surface area of the starting fumed material aggregates before aerosolizing. Thus, when aerosolized, the greater fractal dimensions of the fumed materials are preserved. The greater fractal dimensions of these fumed materials may result in an increased surface area of the catalyst particles compared to catalyst particles produced from non-fumed precursors, such as mesoporous silica or aluminum nitrate. Non-fumed catalyst support materials have lesser fractal dimensions, which may result in producing catalyst particles having greater density and reduced surface area compared to catalyst particles made with fumed catalyst support materials.

Referring now to FIG. 8, the BET surface areas for catalyst particles having decreasing weight ratios of fumed silica (fumed material) to alumina (non-fumed material) are graphically depicted. Reference number 802 refers to the BET surface area of AEROSIL® 380 fumed silica marketed by Evonik, prior to aerosolizing the fumed silica to form the catalyst support particles. The AEROSIL® 380 fumed silica precursor, prior to aerosolizing, has a BET surface area of 380 square meters per gram ($m^2/g$). FIG. 8 also shows the BET surface area of different catalyst support particles with increasing amounts of non-fumed alumina, which are indicated by reference numbers 804, 806, 808, 810, 812, and 814. As shown in FIG. 8, the catalyst support particles made from 100 wt. % fumed silica precursor and no alumina exhibits a catalyst particle surface area 804 that is comparable to the BET surface area of the starting AEROSIL® 380, prior to aerosolizing. As the weight percent of the non-fumed alumina increases through catalyst support particles 806, 808, 810, 812, and 814, the BET surface area of the catalyst particle decreases. FIG. 9 provides microphotographs of the catalyst particles made with increasing concentrations of non-fumed alumina. In FIG. 9, the ratios of fumed silica to non-fumed alumina for each of the catalyst particles are as follows: (a) 100:0, (b) 80:20, (c) 60:40, (d) 40:60, (e) 20:80, and (f) 0:100. Not intending to be limited by theory, it is believed that the aluminum nitrate precursor to the alumina reacts and densifies during the aerosol process to at least partially fill in the porosity of the fumed silica aggregates, thereby decreasing the BET surface area of the catalyst support.

The catalyst support may include catalyst support materials that have a high surface area. The catalyst support may have a surface area sufficient to enable reactants to efficiently pass through the catalyst support to access reactive sites on the preformed catalyst material. Efficient passage of reactants through the catalyst support may prevent limitation of the reaction kinetics by mass transfer of reactants through the catalyst support material. For example, in some embodiments, the composite catalyst may be a multi-functional catalyst for producing propene from 2-butene through metathesis, isomerization, and cracking and may include a zeolite as the preformed catalyst material and fumed silica as the catalyst support. The fumed silica catalyst support may have a surface area sufficient for 2-butene, propene, hexene, and other larger olefins to efficiently pass through the fumed silica to reach catalytically active sites on the zeolite for cracking the olefins into smaller olefins. If the average surface area of the catalyst support is too small, then the reactants may be unable to efficiently pass through the catalyst support to access catalytically active sites on the preformed catalyst material (zeolite). In this case, the reaction may become limited by mass transfer of the reactants through the catalyst support. In some embodiments, the catalyst support may have a surface area of from 100 $m^2/g$ to 800 $m^2/g$, such as from 100 $m^2/g$ to 700 $m^2/g$, from 100 $m^2/g$ to 500 $m^2/g$, from 100 $m^2/g$ to 300 $m^2/g$, from 200 $m^2/g$ to 800 $m^2/g$, from 200 $m^2/g$ to 700 $m^2/g$, from 200 $m^2/g$ to 500 $m^2/g$, from 300 $m^2/g$ to 800 $m^2/g$, from 300 $m^2/g$ to 700 $m^2/g$, from 300 $m^2/g$ to 500 $m^2/g$, or from 500 $m^2/g$ to 800 $m^2/g$.

The catalyst support material may have an average pore size that is sufficient to enable reactants to pass through the catalyst support material to access catalytically active sites on the preformed catalyst material (zeolite). If the average pore size of the catalyst support material is too small, then the reactants may not be able to pass through the catalyst support material to reach the catalytically active sites on the preformed active material. However, if the average pore size is too great, then the catalyst support material may not effectively bind the preformed catalyst material within the catalyst support material. In some embodiments, the catalyst support material may have an average pore size of from 2.5 nm to 40 nm. For example, in some embodiments, the catalyst support particle may have an average pore size of from 2.5 nm to 20 nm, from 2.5 nm to 4.5 nm, or from 12 nm to 18 nm.

The catalyst support material may also have an average pore volume sufficient to enable reactants to pass through the catalyst support material to access catalytically active sites on the preformed catalyst material (zeolite). The average pore volume may be a function of the pore size as well as the pore density. For a given average pore size, if the average pore volume of the catalyst support material is too small, then the number of pathways through the catalyst support material to the catalytically active sites on the preformed catalyst material may be less, resulting in limiting the volume flow of reactants to the catalytically active sites on the surfaces of the preformed catalyst material, which may limit the reaction rate achievable by the preformed catalyst material. In some embodiments, the catalyst support material may have an average pore volume of greater than or equal to 0.600 cubic centimeters per gram (cm$^3$/g). For example, in some embodiments, the catalyst support material may have an average pore volume of from 0.600 cm$^3$/g to 2.5 cm$^3$/g, from 0.600 cm$^3$/g to 1.5 cm$^3$/g, from 0.600 cm$^3$/g to 1.3 cm$^3$/g, from 0.600 cm$^3$/g to 0.800 cm$^3$/g, from 0.600 cm$^3$/g to 0.700 cm$^3$/g, or from 0.900 cm$^3$/g to 1.3 cm$^3$/g.

In some embodiments, an amount of the catalyst support material in the composite catalyst may enable the catalyst support material to form agglomerates encapsulating the preformed catalyst material. The amount of the catalyst support material in the composite catalyst may enable the catalyst support material to provide sufficient surface area for reaction of reactants with the catalytically active compound supported by the catalyst support material. In some embodiments, the composite catalyst may include from 20 wt. % to 95 wt. % preformed catalyst material, based on the total weight of the composite catalyst. In some embodiments, the composite catalyst may include from 20 wt. % to 90 wt. %, from 20 wt. % to 80 wt. %, from 20 wt. % to 70 wt. %, from 20 wt. % to 60 wt. %, from 30 wt. % to 95 wt. %, from 30 wt. % to 90 wt. %, from 30 wt. % to 80 wt. %, from 30 wt. % to 70 wt. %, from 30 wt. % to 60 wt. %, from 50 wt. % to 95 wt. %, from 50 wt. % to 90 wt. %, from 50 wt. % to 80 wt. %, from 50 wt. % to 70 wt. %, from 60 wt. % to 95 wt. %, from 60 wt. % to 90 wt. %, or from 60 wt. % to 80 wt. % catalyst support material based on the total weight of the composite catalyst.

As previously described, the composite catalyst may have at least one catalytically active compound supported by the catalyst support material. The catalytically active compound is different than the preformed catalyst material and the catalyst support material. The catalytically active compounds may include catalysts that have catalytic activity to promote one or more than one of metathesis reactions, isomerization, hydrogenation, demetallization, desulfurization, denitrogenation, other reactions, or combinations of these functions. The catalytically active compound may also be functional to remove contaminants and catalyst poisons from a reactant stream. In some embodiments, the catalytically active compounds may include a metathesis catalyst. In other embodiments, the catalytically active compound may include an isomerization catalyst.

In some embodiments, the catalytically active compound may be a metal, metal oxide, other catalytically active compound, or combinations of these. In some embodiments, the catalytically active compound may be a metal, such as platinum, gold, palladium, rhodium, iridium, chromium, other metal, or combinations of these. Alternatively, the catalytically active compound may include a metal oxide, such as one or more than one oxide of a metal from Groups 6-10 of the IUPAC Periodic Table. In some embodiments, the metal oxide may include at least one oxide of molybdenum, rhenium, tungsten, manganese, titanium, cerium, or any combination of these. In some embodiments, the metal oxide may be tungsten oxide. The morphology, type, and amount of the catalytically active compound deposited on the surface of the catalyst support may determine the catalytic activity of the catalyst. In some embodiments, the catalytically active compound may be magnesium oxide (MgO).

In some embodiments, the composite catalyst may include a plurality of catalytically active compounds supported by the catalyst support material. For example, in some embodiments, the composite catalyst may have 1, 2, 3, 4, 5, 6, or more than 6 catalytically active compounds. Theoretically, the number of different catalytically active compounds that can be incorporated into the composite catalyst may be unlimited. However, the number of different catalytically active compounds that can be included in the composite catalyst may be limited by the type of reactions that can be conducted simultaneously. The number of different catalytically active compounds may also be limited by reactions that must be conducted sequentially. The number of different catalytically active compounds may also be limited by catalyst poisoning considerations.

In some embodiments, the catalytically active compounds may be dispersed throughout the catalyst support. At least a portion of the catalytically active compounds may be accessible at the surfaces of the catalyst support. Alternatively, in other embodiments, the catalytically active compound may be deposited on the surfaces of the catalyst accessible to vapors and gases. The catalytically active compound may be deposited on the surfaces of the catalyst support, the preformed catalyst material, or both.

The composite catalyst may have an amount of the catalytically active compound sufficient for the composite catalyst to exhibit the functionality of the catalytically active compound. For example, in some embodiments, the composite catalyst may include an amount of tungsten oxide sufficient for the composite catalyst to conduct metathesis reactions of olefins. In some embodiments, the composite catalyst may have from 0.1 wt. % to 20 wt. % catalytically active compound. For example, in some embodiments, the composite catalyst may have from 0.1 wt. % to 16 wt. %, from 0.1 wt. % to 12 wt. %, from 0.1 wt. % to 8 wt. %, from 0.1 wt. % to 4 wt. %, from 1 wt. % to 20 wt. %, from 1 wt. % to 16 wt. %, from 1 wt. % to 12 wt. %, from 1 wt. % to 8 wt. %, from 1 wt. % to 4 wt. %, from 4 wt. % to 20 wt. %, from 4 wt. % to 16 wt. %, from 4 wt. % to 12 wt. %, from 4 wt. % to 8 wt. %, from 8 wt. % to 20 wt. %, from 8 wt. % to 16 wt. %, from 8 wt. % to 12 wt. %, from 12 wt. % to 20 wt. %, from 12 wt. % to 16 wt. %, or from 16 wt. % to 20 wt. % catalytically active compound, based on the total weight of the composite catalyst.

The composite catalyst is a multi-functional catalyst that combines two or more distinct catalyst materials with different catalytic functionalities into a single composite catalyst particle. The composite catalyst may have a weight ratio of the preformed catalyst material to the sum of the catalyst support material and catalytically active compounds of from 5:1 to 1:20, from 5:1 to 1:15, from 5:1 to 1:10, from 5:1 to 1:5, from 5:1 to 1:1, from 2:1 to 1:20, from 2:1 to 1:15, from 2:1 to 1:10, from 2:1 to 1:5, from 2:1 to 1:1, from 1:1 to 1:20, from 1:1 to 1:15, from 1:1 to 1:10, from 1:1 to 1:5, from 1:2 to 1:20, from 1:2 to 1:15, from 1:2 to 1:10, from 1:2 to 1:5, from 1:5 to 1:20, from 1:5 to 1:15, from 1:5 to 1:10, from 1:10 to 1:20, from 1:10 to 1:15, or from 1:15 to 1:20.

The composite catalyst may have an overall weight ratio of silica to alumina of from 100:1 to 6000:1. For example, the composite catalyst may have an overall weight ratio of silica to alumina of from 100:1 to 4000:1, from 100:1 to 2000:1, from 100:1 to 1000:1, from 100:1 to 500:1, from 500:1 to 6000:1, from 500:1 to 4000:1, from 500:1 to 2000:1, from 500:1 to 1000:1, from 1000:1 to 6000:1, from 1000:1 to 4000:1, from 1000:1 to 2000:1, from 2000:1 to 6000:1, from 2000:1 to 4000:1, or from 4000:1 to 6000:1. The overall weight ratio of silica to alumina in the composite catalyst may depend on the weight ratio of silica to alumina in the preformed catalyst material, the weight ratio of silica to alumina in the catalyst support material, and the weight ratio of the preformed catalyst material to the catalyst support material in the composite catalyst. In some embodiments, the alumina composition of the preformed catalyst material may be modified in conjunction with the weight ratio of the preformed catalyst material to the catalyst support material weight ratio to maintain the overall weight ratio of silica to alumina in the composite catalyst in a range of from 2000:1 to 6000:1, or about 4000:1.

The catalyst support material may form an open and porous support structure surrounding the particles of the preformed catalyst material, due to the high fractal dimensions of the fumed materials used for the catalyst support precursor. Void spaces in the catalyst support material may provide access to the catalytically active sites on the preformed catalyst material surrounded by the catalyst support material and to the catalytically active material dispersed throughout the catalyst support material.

In some embodiments, the composite catalyst may have an cumulative pore volume that is greater than the cumulative pore volume of the preformed catalyst material. In some embodiments, the cumulative pore volume of the composite catalyst may be greater than the cumulative pore volume of a metathesis catalyst produced by aerosolizing the catalyst support precursor and catalytically active compound precursor without the preformed catalyst material. In some embodiments, the composite catalyst may have a cumulative pore volume of greater than or equal to 0.600 cubic centimeters per gram ($cm^3/g$), or greater than or equal to 0.700 $cm^3/g$. For example, in some embodiments, the catalyst support material may have a cumulative pore volume of from 0.600 $cm^3/g$ to 2.5 $cm^3/g$, from 0.600 $cm^3/g$ to 1.5 $cm^3/g$, from 0.600 $cm^3/g$ to 1.3 $cm^3/g$, from 0.700 $cm^3/g$ to 2.5 $cm^3/g$, from 0.700 $cm^3/g$ to 1.5 $cm^3/g$, or from 0.700 $cm^3/g$ to 1.3 $cm^3/g$.

The composite catalyst may have an average particle size from 25 nanometers (nm) to 50 microns (μm). For example, in some embodiments, the composite catalyst may have an average particle size of from 25 nm to 25 μm, from 25 nm to 10 μm, from 25 nm to 5 μm, from 25 nm to 1 μm, from 50 nm to 50 μm, from 50 nm to 25 μm, from 50 nm to 10 μm, from 50 nm to 5 μm, from 50 nm to 1 μm, from 500 nm to 50 μm, from 500 nm to 25 μm, from 500 nm to 10 μm, from 500 nm to 5 μm, from 500 nm to 1 μm, from 1 μm to 50 μm, from 1 μm to 25 μm, from 1 μm to 10 μm, from 10 μm to 50 μm, from 10 μm to 25 μm, or from 25 μm to 50 μm. The average particle size of the composite catalyst may be modified by changing the composition of the catalyst support precursor mixture during synthesis according to the methods described subsequently in this disclosure. For example, in some embodiments, the composite catalyst may have an average particle size of from 1 μm to 10 μm. In other embodiments, the composite catalyst may have an average particle size of from 25 nm to 5 μm.

In some embodiments, the composite catalyst may have an average surface area of from 100 meters squared per gram ($m^2/g$) to 700 $m^2/g$. In other embodiments, the composite catalyst may have a surface area of from 450 $m^2/g$ to 600 $m^2/g$, from 250 $m^2/g$ to 350 $m^2/g$, from 275 $m^2/g$ to 325 $m^2/g$, or from 275 $m^2/g$ to 300 $m^2/g$. In some embodiments, the composite catalyst may have a pore size distribution of from 2.5 nanometers (nm) to 40 nm and a total pore volume of at least 0.600 cubic centimeters per gram ($cm^3/g$). Without being bound by theory, it is believed that the pore size distribution and pore volume are sized to achieve better catalytic activity and reduced blocking of pores by metal oxides, whereas smaller pore volume and pore size catalyst systems are susceptible to pore blocking, which may reduce catalytic activity. In some embodiments, the composite catalyst may have a pore size distribution of from 2.5 nm to 40 nm, from 2.5 nm to 20 nm, from 2.5 nm to 4.5 nm, from 2.5 nm to 3.5 nm, from 8 nm to 18 nm, or from 12 nm to 18 nm. In some embodiments, the composite catalyst may have a total pore volume of from 0.600 $cm^3/g$ to 2.5 $cm^3/g$, from 0.600 $cm^3/g$ to 1.5 $cm^3/g$, from 0.600 $cm^3/g$ to 1.3 $cm^3/g$, from 0.600 $cm^3/g$ to 0.800 $cm^3/g$, from 0.600 $cm^3/g$ to 0.700 $cm^3/g$, or from 0.900 $cm^3/g$ to 1.3 $cm^3/g$.

In some embodiments, the catalyst support material may form unbonded agglomerates surrounding the preformed catalyst material. In the unbonded agglomerate, the aggregates of the catalyst support material may not be bonded to each other and may not be bonded to the particles of the preformed catalyst material. As used in this disclosure, the term "aggregates" refers to small individual particles of a constituent prior to synthesizing the composite catalyst, and the term "agglomerate" refers to the three-dimensional structure formed from the particles of the preformed catalyst material and the catalyst support material. In other embodiments, the aggregates of the catalyst support material may be chemically bound to the preformed catalyst material, other aggregates of the catalyst support material, or both. This may be accomplished by increasing the temperature in the heating zone of the aerosol process for making the composite catalyst or by introducing additional precursors, such as bonding agents, to promote chemical bonding between the materials.

In some embodiments, the composite catalyst may be catalytically active to produce propene from 2-butene through combinations of butene isomerization reactions, olefin metathesis reactions, and cracking reactions. For example, the composite catalyst may include from 5 wt. % to 50 wt. % MFI structured zeolite as the preformed catalyst material, 20 wt. % to 80 wt. % fumed silica as the catalyst support material, and from 0.1 wt. % to 20 wt. % tungsten oxide as the catalytically active compound distributed throughout the fumed silica.

The following methods and systems are described in the context of synthesizing a multi-functional composite catalyst having at least metathesis and cracking functionality for producing propene from 2-butene. The composite catalysts may also have isomerization functionality. However, it is understood that the methods and system may be utilized to synthesize multi-functional composite catalysts having various other catalytic functionalities, such as hydrogenation, demetalization, desulfurization, denitrogenation, other reactions, or combinations of these for example.

A method of synthesizing the composite catalyst having the catalytically active compound deposited on the surface of the catalyst support in accordance with at least one embodiment of this disclosure includes generating an aerosolized catalyst precursor mixture by aerosolizing a catalyst precursor mixture comprising the preformed catalyst material, a catalyst support precursor, at least one catalytically active compound precursor, and a diluent. The method further includes drying the aerosolized catalyst precursor mixture to produce the composite catalyst. The aerosol processing method may be a continuous process to continuously produce the catalyst from the preformed catalyst material, catalyst support precursor, and the catalytically active compound precursor.

The aerosol process method of making the multi-functional composite catalyst does not require the formation of a sol-gel, and therefore does not require sustained mixing, to convert the solution to a gel. The aerosol process method can be a continuous process for making the multi-functional composite catalyst and can be used to combine multiple combinations of catalysts in several different types of multi-functional composite catalyst. Additionally, the aerosol process of the present disclosure may enable fine-tuning of the composition and properties of the multi-functional composite catalyst to enhance performance of the catalyst. As will be described subsequently in this disclosure, the composition and properties of the multi-functional composite catalyst may be fine-tuned by controlling or adjusting the composition of a catalyst precursor mixture, the operating conditions of the aerosolizing process, and operation of the heating zone(s).

Referring to FIG. 1, an aerosol processing system 100 for synthesizing the composite catalyst is depicted. As shown in FIG. 1, the aerosol processing system 100 includes a vessel 102 for mixing the catalyst support precursor 104, the preformed catalyst material 105, the diluent 106, and the catalytically active compound precursor 107 to form the catalyst precursor mixture 108. The aerosol processing system 100 further includes an aerosolizing unit 110 and a heating zone 120 downstream of the aerosolizing unit 110. The catalyst precursor mixture 108 may be passed to the aerosolizing unit 110. The aerosolizing unit 110 aerosolizes the catalyst precursor mixture 108 into a plurality of droplets of the catalyst precursor mixture 108, referred to in this disclosure as the aerosolized catalyst precursor mixture 114. A carrier gas 112 may be introduced to the aerosolizing unit 110 to convey the aerosolized catalyst precursor mixture 114 out of the aerosolizing unit 110 and through the heating zone 120, in which the droplets of the aerosolized catalyst precursor mixture 114 are dried, reacted, or both to form a plurality of solid composite catalyst particles 144. Stream 126 passing out of the heating zone 120 includes the solid composite catalyst particles 144 aerosolized in gases 146. The gases 146 may include the carrier gases 112, any volatile constituents of the catalyst precursor mixture 108 that volatilize in the heating zone 120, or gaseous reaction products from catalyst precursor decomposition. Stream 126 may be passed through an in-line analyzer 150 or passed to a separator 140, where the composite catalyst particles 144 may be separated from the gases 146.

The catalyst precursor mixture 108 may include the catalyst support precursor 104, the preformed catalyst material 105, the diluent 106, and at least one catalytically active compound precursor 107. The preformed catalyst material 105 may include any of the preformed catalyst materials previously described in this disclosure. The catalyst precursor mixture 108 may include from 5 wt. % to 50 wt. % preformed catalyst material 105 based on the dry weight of the catalyst precursor mixture 108. The "dry weight" of the catalyst precursor mixture 108 refers to the total weight of the catalyst precursor mixture 108 minus the total weight of diluent in the catalyst precursor mixture 108.

The catalyst support precursor 104 may include any of the catalyst support materials previously described in this disclosure. In some embodiments, the catalyst support precursor 104 may include a silica precursor such as fumed silica, an alumina precursor such as fumed alumina or a soluble aluminum salt, a titania precursor such as fumed titania, other catalyst support precursor, or combinations of these. In some embodiments, the silica precursor may include fumed silica. In embodiments, the catalyst support precursor 104 may include a plurality of precursor materials, such as a combination of silica precursors and alumina precursors for example. In some embodiments, the catalyst support precursor 104 may include from 0.1 weight percent (wt. %) to 99.9 wt. % fumed silica, based on the total weight of the catalyst support precursor 104 prior to combining the catalyst support precursor 104 into the catalyst precursor mixture 108. In embodiments, the catalyst support precursor 104 may include from 0.1 wt. % to 95 wt. %, from 0.1 to 90 wt. %, from 0.1 wt. % to 75 wt. %, from 0.1 wt. % to 50 wt. %, from 0.1 wt. % to 25 wt. %, from 0.1 wt. % to 10 wt. %, from 10 wt. % to 99.9 wt. %, from 10 wt. % to 95 wt. %, from 10 wt. % to 90 wt. %, from 10 wt. % to 75 wt. %, from 10 wt. % to 50 wt. %, from 10 wt. % to 25 wt. %, from 25 wt. % to 99.9 wt. %, from 25 wt. % to 95 wt. %, from 25 wt. % to 90 wt. %, from 25 wt. % to 75 wt. %, from 25 wt. % to 50 wt. %, from 50 wt. % to 99.9 wt. %, from 50 wt. % to 95 wt. %, from 50 wt. % to 90 wt. %, from 50 wt. % to 75 wt. %, from 75 wt. % to 99.9 wt. %, from 75 wt. % to 95 wt. %, from 75 wt. % to 90 wt. %, or from 90 wt. % to 99.9 wt. % fumed silica, based on the total weight of the catalyst support precursor 104 prior to combining the catalyst support precursor 104 with the catalyst precursor mixture 108.

Examples of alumina precursors may include, but are not limited to, aluminum nitrate ($Al(NO_3)_3$), fumed alumina, aluminum salts, such as $AlCl_3$, $AlPO_4$, or $Al_2(SO_4)_3$ and their hydrates, other alumina precursors, or combinations of these. In some embodiments, the alumina precursor may comprise fumed alumina. In some embodiments, the catalyst support precursor 104 may include from 0.0 wt. % to 99.8 wt. % alumina precursor, based on the total weight of the catalyst support precursor 104 prior to combining the catalyst support precursor 104 into the catalyst precursor mixture 108. In other examples, the catalyst support precursor 104 may include from 0.0 wt. % to 95 wt. %, from 0.0 to 90 wt. %, from 0.0 wt. % to 75 wt. %, from 0.0 wt. % to 50 wt. %, from 0.0 wt. % to 25 wt. %, from 0.0 wt. % to 10 wt. %, from 0.1 wt. % to 99.8 wt. %, from 0.1 wt. % to 95 wt. %, from 0.1 wt. % to 90 wt. %, from 0.1 wt. % to 75 wt. %, from 0.1 wt. % to 50 wt. %, from 0.1 wt. % to 25 wt. %, from 10 wt. % to 99.8 wt. %, from 10 wt. % to 95 wt. %, from 10 wt. % to 90 wt. %, from 10 wt. % to 75 wt. %, from 10 wt. % to 50 wt. %, from 25 wt. % to 99.8 wt. %, from 25 wt. % to 95 wt. %, from 25 wt. % to 90 wt. %, from 50 wt. % to 99.8 wt. %, from 50 wt. % to 95 wt. %, from 50 wt. % to 90 wt. %, from 75 wt. % to 99.8 wt. %, or from 75 wt. % to 95 wt. % alumina precursor, based on the total weight of the catalyst support precursor 104 prior to combining the catalyst support precursor 104 into the catalyst precursor mixture 108.

In some embodiments, the catalyst support precursor 104 may include fumed titania. The catalyst support precursor 104 may include from 0.1 weight percent (wt. %) to 99.9 wt. % fumed titania, based on the total weight of the catalyst support precursor 104 prior to combining the catalyst support precursor 104 into the catalyst precursor mixture 108. In embodiments, the catalyst support precursor 104 may include from 0.1 wt. % to 95 wt. %, from 0.1 to 90 wt. %, from 0.1 wt. % to 75 wt. %, from 0.1 wt. % to 50 wt. %, from 0.1 wt. % to 25 wt. %, from 0.1 wt. % to 10 wt. %, from 10 wt. % to 99.9 wt. %, from 10 wt. % to 95 wt. %, from 10 wt. % to 90 wt. %, from 10 wt. % to 75 wt. %, from 10 wt. % to 50 wt. %, from 10 wt. % to 25 wt. %, from 25 wt. % to 99.9 wt. %, from 25 wt. % to 95 wt. %, from 25 wt. % to 90 wt. %, from 25 wt. % to 75 wt. %, from 25 wt. % to 50 wt. %, from 50 wt. % to 99.9 wt. %, from 50 wt. % to 95 wt. %, from 50 wt. % to 90 wt. %, from 50 wt. % to 75 wt. %, from 75 wt. % to 99.9 wt. %, from 75 wt. % to 95 wt. %, from 75 wt. % to 90 wt. %, or from 90 wt. % to 99.9 wt. % fumed titania, based on the total weight of the catalyst support precursor 104 prior to combining the catalyst support precursor 104 with the catalyst precursor mixture 108.

The catalyst precursor mixture 108 may include from 20 wt. % to 95 wt. % catalyst support precursor 104 based on the dry weight of the catalyst precursor mixture 108. Again, dry weight refers to the weight of the catalyst precursor mixture 108 without the diluent. For example, in some embodiments, the catalyst precursor mixture 108 may include from 20 wt. % to 90 wt. %, from 20 wt. % to 85 wt. %, from 20 wt. % to 80 wt. %, from 20 wt. % to 70 wt. %, from 20 wt. % to 60 wt. %, from 30 wt. % to 95 wt. %, from 30 wt. % to 90 wt. %, from 30 wt. % to 85 wt. %, from 30 wt. % to 80 wt. %, from 30 wt. % to 70 wt. %, from 50 wt. % to 95 wt. %, from 50 wt. % to 90 wt. %, from 50 wt. % to 85 wt. %, from 50 wt. % to 80 wt. %, from 50 wt. % to 70 wt. %, from 70 wt. % to 95 wt. %, from 70 wt. % to 90 wt. %, from 70 wt. % to 85 wt. %, or from 80 wt. % to 95 wt. % catalyst support precursor 104, based on the dry weight of the catalyst precursor mixture 108.

In some embodiments, the catalytically active compound precursor 107 may be a metal, such as platinum, gold, palladium, rhodium, iridium, chromium, other metal, or combinations of these. In some embodiments, the catalytically active compound precursor 107 may be a metal salt that can be solubilized in the diluent 106. In some embodiments, the catalytically active compound precursor 107 may include an oxometallate precursor. In some embodiments, the oxometallate precursor may be a metal oxide precursor of one or more oxides of a metal from the Groups 6-10 of the IUPAC Periodic Table. The metal oxide may be at least one oxide of molybdenum, rhenium, tungsten, manganese, titanium, cerium, or any combination of these. Alternatively, in some embodiments, the oxometallate precursor may be a tungstate precursor. Examples of tungstate precursors may include, but are not limited to, ammonium metatungstate $((NH_4)_6H_2W_{12}O_{40})$, tungstic acid, phosphotungstic acid, sodium tungstate, other tungstate precursor, or combinations of these. In some embodiments, the tungstate precursor may comprise ammonium metatungstate $((NH_4)_6H_2W_{12}O_{40})$. In some embodiments, the metal oxide may be a tungsten oxide, such as tungsten (IV) oxide, tungsten (VI) oxide, other tungsten oxides, or combinations of tungsten oxides. In some embodiments, the metal oxide is tungsten oxide $(WO_3)$. In some embodiments, the metal oxide may include magnesium oxide (MgO). In some embodiments, the catalyst precursor mixture 108 may include a plurality of catalytically active compound precursors 107 to produce a composite catalyst having a plurality of catalytically active compounds distributed throughout the catalyst support material.

In some embodiments, the catalyst precursor mixture 108 may include from 0.1 wt. % to 20 wt. % catalytically active compound precursors 107, based on the dry weight of the catalyst precursor mixture 108. As previously discussed, the dry weight of the catalyst precursor mixture 108 refers to the weight of the catalyst precursor mixture 108 without the diluent 106. In other embodiments, the catalyst precursor mixture 108 may include from 0.1 wt. % to 16 wt. %, from 0.1 wt. % to 12 wt. %, from 0.1 wt. % to 8 wt. %, from 0.1 wt. % to 4 wt. %, from 1 wt. % to 20 wt. %, from 1 wt. % to 16 wt. %, from 1 wt. % to 12 wt. %, from 1 wt. % to 8 wt. %, from 1 wt. % to 4 wt. %, from 4 wt. % to 20 wt. %, from 4 wt. % to 16 wt. %, from 4 wt. % to 12 wt. %, from 4 wt. % to 8 wt. %, from 8 wt. % to 20 wt. %, from 8 wt. % to 16 wt. %, from 8 wt. % to 12 wt. %, from 12 wt. % to 20 wt. %, from 12 wt. % to 16 wt. %, or from 16 wt. % to 20 wt. % catalytically active compound precursors 107, based on the dry weight of the catalyst precursor mixture 108.

In some embodiments, the catalyst precursor mixture 108 may include from 20.0 wt. % to 80.0 wt. % catalyst support precursor 104, from 5.0 wt. % to 50.0 wt. % preformed catalyst material 105, and from 0.1 wt. % to 20.0 wt. % catalytically active compound precursors 107, based on the dry weight of the catalyst precursor mixture 108.

The diluent 106 may be water, an organic solvent, or a combination of water and at least one organic solvent. Example organic solvents may include methanol, ethanol, acetone, or a combination of solvents. In some embodiments, the diluent 106 may be water such that the catalyst precursor mixture 108 is an aqueous catalyst precursor mixture. In other embodiments, the diluent 106 may include a combination of water and at least one organic solvent. In some embodiments, the catalyst precursor mixture 108 may be lacking a surfactant. Inclusion of a surfactant in the catalyst precursor mixture 108 may require an additional calcination step to remove residual surfactant and prepare the composite catalyst. In some cases, the presence of a surfactant in the catalyst precursor mixture 108 may result in an undesired residue on the composite catalyst, which may degrade the performance of the composite catalyst, may be toxic or hazardous to health, or both.

The catalyst precursor mixture 108 may have an amount of the diluent 106 sufficient to aerosolize the catalyst precursor mixture 108. The catalyst precursor mixture 108 may have an amount of diluent 106 sufficient to produce a desired average particle size of the composite catalyst particles made by the aerosol process. In some embodiments, the catalyst precursor mixture 108 may include from 85 wt. % to 99 wt. % diluent 106 based on the total weight of the catalyst precursor mixture. For example, in some embodiments, the catalyst precursor mixture 108 may include from 85 wt. % to 97 wt. %, from 85 wt. % to 95 wt. %, from 85 wt. % to 90 wt. %, from 90 wt. % to 99 wt. %, from 90 wt. % to 97 wt. %, from 90 wt. % to 95 wt. %, from 93 wt. % to 99 wt. %, from 93 wt. % to 97 wt. %, or from 95 wt. % to 99 wt. % diluent 106 based on the total weight of the catalyst precursor mixture 108.

In some embodiments, the catalyst precursor mixture 108 may optionally include one or a plurality of dopants (not shown). The catalyst precursor mixture 108 may include a dopant to modify one or more than one characteristic or property of the catalyst support particles 114 formed from the catalyst support precursor mixture 108. For example, a binder may be added to the catalyst precursor mixture 108 to promote chemical bonding between the catalyst support precursors 104 and the preformed catalyst material 105. Additionally, dopants may include inert constituents, sacrificial constituents, or both, in the catalyst precursor mixture 108. Non-limiting examples of inert and sacrificial constituents may include polystyrene latex, other polymers, or combinations of polymers. When heated to high temperatures, the polystyrene latex burns off, leaving pores where the polystyrene latex was previously. These inert and sacrificial constituents may be used to modify the surface area of the composite catalyst particles 144. In embodiments, one or more than one dopant may be included in the catalyst precursor mixture 108 so that the dopant(s) are thus included in and distributed throughout the composite catalyst particles 144 during the aerosol processing.

The catalyst precursor mixture 108 may be formed as a suspension of solids in a liquid phase, the liquid phase comprising at least the diluent 106. The solids may include the preformed catalyst material 105, the catalyst support precursor 104, the catalytically active compound precursor 107, dopant, or combinations of these. For example, the preformed catalyst material 105 and fumed catalyst support precursors 104, such as fumed silica, fumed alumina, fumed titania, fumed silica-alumina, or combinations of these, form a solid suspension in the diluent for the catalyst support precursor mixture 108. Alternatively, in some embodiments, the catalytically active compound precursor 107 may be a salt, such as a metal salt, that is at least partially soluble in the diluent. In this case, the solid preformed catalyst material 105, solid catalyst support precursors 104, and other solid constituents form a solid suspension of solid particles in a solution comprising the diluent and the soluble portion of the catalytically active compound precursor 107.

The catalyst precursor mixture 108 may have a total quantity of catalyst precursors sufficient so that the diluent is removed to form the solid composite catalyst particles 144 from the aerosolized catalyst precursor mixture 114 during the residence time of the aerosolized catalyst precursor mixture 114 in the heating zone 120. The total quantity of catalyst precursors in the catalyst precursor mixture 108 refers to the sum of the quantities of the catalyst support precursor 104, the preformed catalyst material 105, the catalytically active compound precursor 107, and any optional dopants in the catalyst precursor mixture 108. In embodiments, the catalyst precursor mixture 108 may include from 1 wt. % to 20 wt. % total precursors, based on the total weight of the catalyst support precursor mixture 108. In other embodiments, the catalyst support precursor mixture 108 may include from 1 wt. % to 16 wt. %, from 1 wt. % to 12 wt. %, from 1 wt. % to 8 wt. % from 1 wt. % to 4 wt. %, from 4 wt. % to 20 wt. %, from 4 wt. % to 16 wt. %, from 4 wt. % to 12 wt. %, from 4 wt. % to 8 wt. %, from 8 wt. % to 20 wt. %, from 8 wt. % to 16 wt. %, from 8 wt. % to 12 wt. %, from 12 wt. % to 20 wt. %, from 12 wt. % to 16 wt. %, or from 16 wt. % to 20 wt. % total catalyst precursors, based on the total weight of the catalyst precursor mixture 108.

In some embodiments, the catalyst precursor mixture 108 may include a weight ratio of preformed catalyst material 105 to the sum of the catalyst support precursor 104 and catalytically active compound precursors 107 of from 1:1 to 1:20, from 1:1 to 1:15, from 1:1 to 1:10, from 1:1 to 1:5, from 1:2 to 1:20, from 1:2 to 1:15, from 1:2 to 1:10, from 1:2 to 1:5, from 1:5 to 1:20, from 1:5 to 1:15, from 1:5 to 1:10, from 1:10 to 1:20, from 1:10 to 1:15, or from 1:15 to 1:20.

As previously discussed, the catalyst precursor mixture 108 may be aerosolized to form an aerosolized catalyst precursor mixture 114, which comprises a plurality of droplets of the catalyst precursor mixture 108 dispersed in the carrier gas 112. As shown in FIG. 1, the catalyst precursor mixture 108 may be aerosolized in the aerosolizing unit 110 to form the aerosolized catalyst precursor mixture 114. A variety of aerosolizing units 110 are envisioned, as long as they generate a liquid spray of droplets. Examples of aerosolizing units 110 may include, but are not limited to, ultrasonic transducers, spray nozzles, other aerosolizing devices, or combinations of these. In some embodiments, the aerosolizing unit 110 may be an ultrasonic transducer. Ultrasonic transducers may be readily scalable and highly controllable.

The type of aerosolizing unit 110 and the specifications of the aerosolizing unit 110 may influence the particle size of the composite catalyst particles 144 by influencing the average droplet size of the aerosolized catalyst precursor mixture 114. For example, an aerosolizing unit 110 configured to produce smaller-sized droplets will generally result in the composite catalyst particles 144 having a smaller average particle size. The type, specifications, or both of the aerosolizing unit 110 may also influence the particle size of the composite catalyst particles 144 by increasing the turbulence of the aerosolized catalyst precursor mixture 114, which may cause some droplets to collide and combine into larger droplets. In some embodiments, the aerosolizing unit 110 may be capable of producing droplets of the catalyst precursor mixture 108 having droplet sizes from 0.1 μm to 100 μm, from 0.1 μm to 20 μm, from 0.5 μm to 100 μm, or from 0.5 μm to 20 μm.

As previously discussed, a carrier gas 112 is introduced to the aerosolizing unit 110. The aerosolized catalyst precursor mixture 114 is aerosolized in the carrier gas 112, which then transports the droplets of the aerosolized catalyst precursor mixture 114 into and through the heating zone 120. In some embodiments, the carrier gas 112 may be air. Alternatively, in other embodiments, the carrier gas 112 may include at least one of nitrogen, argon, helium, or combinations of these gases. In yet further embodiments, the carrier gas 112 may include one or more reactants, dopants, or both for the formation of the composite catalyst particles 144. For example, the carrier gas 112 may include silane ($SiH_4$). The selection of a non-reactive gas or a reactive gas or a combination of both for the carrier gas 112 may depend on the catalyst support precursors 104, catalytically active compound precursors 107, or preformed catalyst material 105 utilized and the desired properties of the composite catalyst.

Referring to FIG. 1, the aerosolized catalyst precursor mixture 114 is passed to and through the heating zone 120 downstream of the aerosolizing unit 110 to form the composite catalyst particles 144. The method of synthesizing the composite catalyst includes drying the aerosolized catalyst precursor mixture 114, reacting the aerosolized catalyst precursor mixture 114, or both in the heating zone 120 to form the plurality of composite catalyst particles 144. The droplets of the aerosolized catalyst precursor mixture 114 are passed to the heating zone 120, where heat from the heating zone 120 causes the droplets of the aerosolized catalyst precursor mixture 114 to form the plurality of composite catalyst particles 144, such as by removing the diluent 106 from the aerosolized catalyst precursor mixture 114. In some embodiments, the heating zone 120 may be a region of a first furnace 122, and the carrier gas 112 may convey the droplets of the aerosolized catalyst precursor mixture 114 through the region of the first furnace 122. Alternatively, the heating zone 120 may comprise a first section of a reaction tube disposed within the first furnace 122, and the carrier gas 112 may convey the droplets of the aerosolized catalyst precursor mixture 114 through the reaction tube 124. In these embodiments in which the system 100 includes the reaction tube 124, the heat from the first furnace 122 may be transferred to the reaction tube 124, conducted through the wall of the reaction tube 124, and then transferred to the droplets of the aerosolized catalyst precursor mixture 114 flowing through the reaction tube 124.

Figure 2:
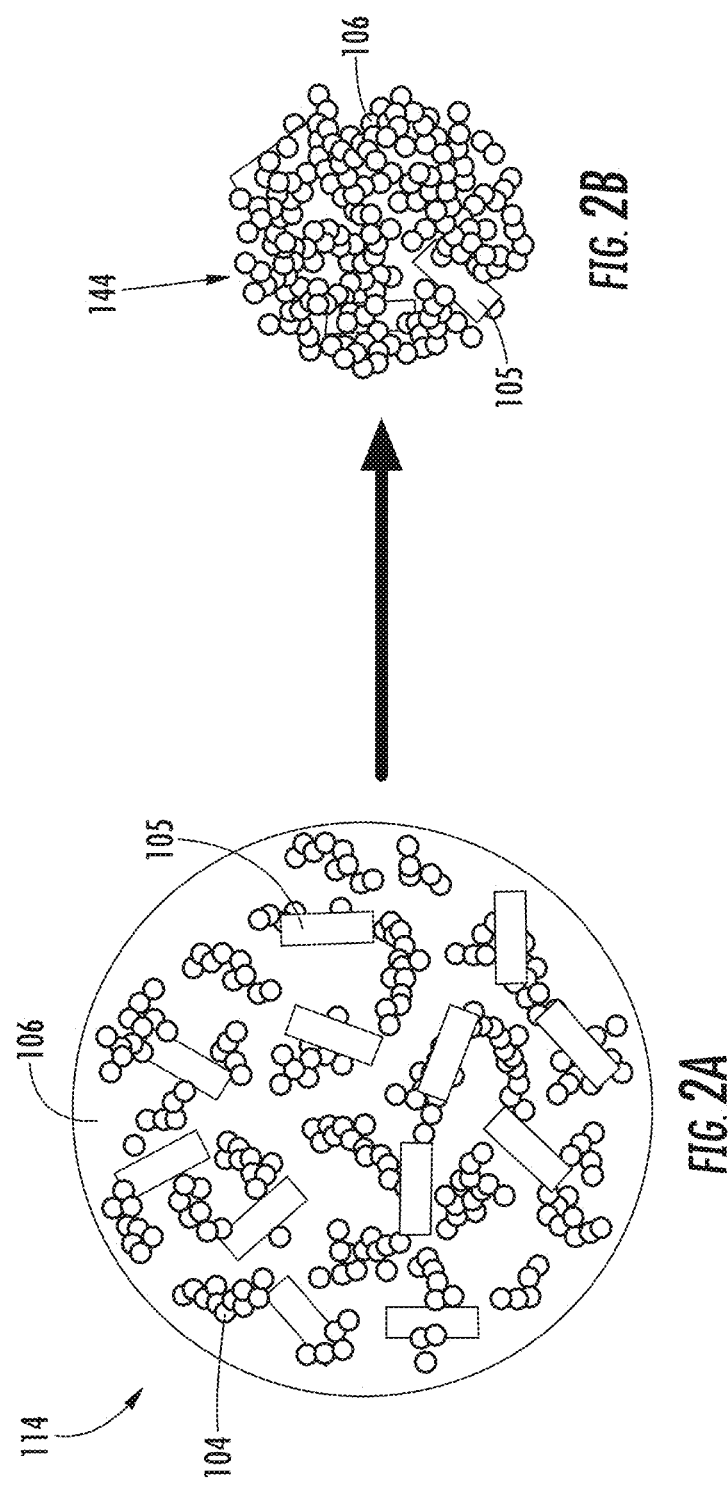
FIG. 2A schematically depicts an aerosolized droplet of a catalyst precursor mixture prior to heating the droplet to form a multi-functional composite catalyst, in accordance with one or more embodiments of the present disclosure.
FIG. 2B schematically depicts a particle of the multi-functional composite catalyst after heating the droplet of FIG. 2A to remove a diluent from the droplet, in accordance with one or more embodiments of the present disclosure.

Referring to FIGS. 2A and 2B, drying of a droplet of the aerosolized catalyst precursor mixture 114 in the heating zone 120 (FIG. 1) to produce the composite catalyst particle 144 is depicted. FIG. 2A illustrates a droplet of the aerosolized catalyst precursor mixture 114 that includes a plurality of aggregates of the catalyst support precursor 104 and aggregates of the preformed catalyst material 105 suspended in the diluent 106. The catalytically active compound precursor 107 is omitted from FIGS. 2A and 2B for purposes of illustration. Heat from the heating zone 120 causes removal of the diluent 106 from the droplet of the aerosolized catalyst precursor mixture 114, such as by vaporization of the diluent 106. As the diluent vaporizes from the droplet of the aerosolized catalyst precursor mixture 114, the volume of the droplet of the aerosolized catalyst precursor mixture 114 decreases and the aggregates of the catalyst support precursor 104 converge to form a three-dimensional support structure surrounding and trapping the aggregates of the preformed catalyst material 105 as shown in FIG. 2B. In some embodiments, the catalyst support precursor 104, a binder compound, or both may react in the heating zone 120 to chemically bond the aggregates of the catalyst support precursor 104 together and to the preformed catalyst material 105 as the diluent 106 vaporizes. In some embodiments, the catalytically active compound precursor 107 may react to form the catalytically active compound dispersed throughout the three-dimensional support structure formed by the catalyst support precursor 104 and the preformed catalyst material 105.

In embodiments, the heating zone 120 may be maintained at a temperature sufficient to vaporize the diluent 106 from the droplets of the aerosolized catalyst precursor mixture 114 to form a plurality of solid composite catalyst particles 144. In embodiments, the heating zone 120 may be maintained at a temperature of from 25° C. to 1500° C. In other embodiments, the first heating zone may be maintained at a temperature of from 25° C. to 1450° C., from 25° C. to 1400° C., from 25° C. to 1300° C., from 200° C. to 1500° C., from 200° C. to 1450° C., from 200° C. to 1400° C., from 200° C. to 1300° C., from 500° C. to 1500° C., from 500° C. to 1450° C., from 500° C. to 1400° C., from 500° C. to 1300° C., from 750° C. to 1500° C., from 750° C. to 1450° C., from 750° C. to 1400° C., from 750° C. to 1300° C., from 1000° C. to 1500° C., 1000° C. to 1450° C., from 1000° C. to 1400° C., from 1300° C. to 1500° C., from 1300° C. to 1400° C., or from 1400° C. to 1500° C. In further embodiments, to merely dry the droplets of the aerosolized catalyst precursor mixture 114, the heating zone 120 may be heated to a temperature from 200° C. to 800° C. If the temperature in the heating zone 120 is too great, the droplets of the aerosolized catalyst precursor mixture 114 may rapidly dry to form a shell structure of the catalyst support precursor 104 rather than solid composite catalyst particles 144. Catalyst shells are less able to withstand the stress and pressures exerted on the catalyst 101 during downstream processing, use, or both compared to the solid composite catalyst particles 144. In some embodiments, the first furnace 122 may include a plurality of heating zones 120 operated at different temperatures.

The residence time of the aerosolized catalyst precursor mixture 114 in the heating zone 120 may be sufficient to produce fully dried and reacted composite catalyst particles 144. In some embodiments, the residence time of the aerosolized catalyst precursor mixture 114 in the heating zone 120 may be from 0.1 seconds to 9 seconds. In other embodiments, the residence time of the aerosolized catalyst precursor mixture 114 in the heating zone 120 may be from 0.1 seconds to 8 seconds, 0.1 second to 6 seconds, from 0.1 second to 4 seconds, from 0.5 second to 9 seconds, from 0.5 seconds to 8 seconds, from 0.5 seconds to 6 seconds, from 0.5 second to 4 seconds, from 1 second to 9 seconds, from 1 second to 8 seconds, from 1 second to 6 seconds, from 1 second to 4 seconds, from 2 seconds to 9 seconds, from 2 seconds to 8 seconds, from 2 seconds to 6 seconds, or from 2 seconds to 4 seconds. If the residence time is of insufficient duration, the droplets of the aerosolized catalyst precursor mixture 114 may not dry sufficiently and may be left unreacted such that the composite catalyst particles 144 are not fully formed. Conversely, if the residence time is too great, energy is wasted and the composite catalyst particles 144 may be lost to the furnace walls or grow too large in size due to collisions with other composite catalyst particles 144. Additionally, drying the droplets of the aerosolized catalyst precursor mixture 114 too rapidly, such as by decreasing the residence time too much, increasing the temperature in the heating zone 120 too much, or both, can lead to composite catalyst shells, which can collapse under further processing, instead of solid composite catalyst particles 144, as previously described.

The feed rate of the aerosolized catalyst precursor mixture 114 into and through the heating zone 120 may be determined by the flowrate of the carrier gas 112. In general, the faster the flowrate of the carrier gas 112, the higher the feed rate of the aerosolized catalyst precursor mixture 114 into the heating zone 120. The carrier gas 112 flowrate may also influence the residence time of the aerosolized catalyst precursor mixture 114 in the heating zone 120. Increasing the carrier gas 112 flowrate may reduce the residence time. Conversely, decreasing the carrier gas 112 flowrate may increase the residence time. In embodiments, the carrier gas 112 flowrate may be sufficient to maintain an aerosolized and fluidized flow of droplets of the aerosolized catalyst precursor mixture 114 through the heating zone 120 but not so much that the residence time of the aerosolized catalyst precursor mixture 114 is not sufficient to fully form the composite catalyst particles 144. In some embodiments, the carrier gas 112 flowrate may be sufficient to achieve a residence time of the aerosolized catalyst precursor mixture 114 in the heating zone 120 as previously described in this disclosure. For embodiments in which the aerosolizing unit 110 comprises one or a plurality of ultrasonic transducers, the carrier gas 112 flowrate may be from 1.25 liters per min (L/min) to 3.75 L/min per transducer. Alternatively, the carrier gas 112 flowrate may be greater than 3.75 L/min or less than 1.25 L/min depending on the size of the heating zone 120, aerosolizing unit 110, or other operation of the aerosol processing system 100.

In embodiments, the aerosol processing system 100 includes the separator 140 for separating the composite catalyst particles 144 from the gases 146 and collecting the composite catalyst particles 144. The gases 146 in which the composite catalyst particles 144 may include the carrier gas 112 as well as volatile constituents of the catalyst precursor mixture 108, such as vaporized diluent or vaporized catalytically active compound precursors for example. The stream 126, which includes the gases 146 and the composite catalyst particles 144 entrained in the gases 146, may pass out of the heating zone 120 and into the separator 140. The method of synthesizing the composite catalyst may include separating the composite catalyst particles 144 from the gases 146 and collecting the composite catalyst particles 144. In some embodiments, the gases 146 may be passed from the separator 140 to the atmosphere without further treatment. Alternatively, the gases 146 exiting the separator 140 may be further processed to recover residual constituents of the process, such as catalytically active compound vapors, organic solvents from the catalyst precursor mixture 108, other reactants or contaminants, or combinations of these. In some embodiments, the gases 146 passed out of the separator 140 may be substantially free of chlorine-containing compounds. As an example, the gases 146 exiting the separator 140 may have less than 0.1 wt. % chlorine-containing compounds. In some embodiments, the stream 126 may be passed from the heating zone 120 to an in-line analyzer 150 and then passed from the in-line analyzer 150 to the separator 140.

In some embodiments, the separator 140 may be a cyclone separator, an electrostatic precipitator, or a filter that is used to separate the composite catalyst particles from the flow of gases 146 exiting the heating zone 120. An example filter may comprise borosilicate fibers bound with polyvinylidene fluoride (PVDF) configured to have a desired efficiency at capturing 0.01 micron (μm) particles. Another example filter may consist of quartz bound with an inorganic resin that can tolerate higher operating temperatures. The filter may also be comprised of any commercially available bag house filter material. In selecting a filter, there is a desire to balance pore size of the filter to sufficiently collect the composite catalyst particles 144 with the resulting pressure increase, which results as the filter collects the composite catalyst particles 144 and at temperatures suitable for collection. As the filter begins to clog and a particle cake forms, the filter becomes a more efficient filter and the pressure starts to rise. In operation, the resulting pressure rise may be used as an indicator of the quantity of composite catalyst particles 144 collected within the filter. Additionally, the filter material may be temperature stable at temperatures greater than or equal to the temperature of stream 126 exiting the heating zone 120 to prevent the filter material from undergoing combustion.

Utilizing the aerosol processing system 100 and aerosol methods previously discussed in this disclosure for producing the multi-functional composite catalyst may enable control of the composition, properties, and characteristics of the multi-functional composite catalyst to customize the catalyst for the conversion of a variety of different compounds. Varying the parameters of the aerosol processing method may control formation of the resulting multi-functional composite catalysts, such as composite catalysts for converting 2-butene to propene through a combination of isomerization, olefin metathesis, and cracking reactions. The multi-functional composite catalysts made from the aerosol processing system 100 and methods may exhibit a range of structural and chemical properties, which may be customized or modified for different conversion reactions. For example, adjusting the composition and structural characteristics of the catalyst support material may influence the isomerization functionality of the composite catalyst. Additionally, controlling the quantity of catalytically active compound distributed throughout the catalyst support material or the structural characteristics of the catalyst support material may enable control of the metathesis functionality of the multi-functional composite catalyst.

The composition of the multi-functional composite catalyst may be controlled by changing the type or concentration of the catalyst support precursors 104, changing the type or concentration of preformed catalyst material 105, changing the types or concentrations of the catalytically active compound precursors 107 in the catalyst precursor mixture 108, adding one or a plurality of dopants to the catalyst precursor mixture 108, and changing the type of carrier gas 112. For example, inclusion of a higher relative concentration of one catalyst support precursor, such as the silica precursor or alumina precursor, in the catalyst precursor mixture 108 will result in a relatively higher concentration of the specific catalyst support precursor 104 in the composite catalyst. In embodiments in which the catalytically active compound precursors 107 include metallates, the metallates may be converted into oxometallates, metal oxides, or both in the heating zone 120, in accordance with the present disclosure by using air as the carrier gas 112. Specifically, air comprises oxygen, which may oxidize the metallates into the oxymetallates, metal oxides, or both. Further, in embodiments with water as the diluent 106, oxygen from the heated water may also be used as an oxygen source to oxidize the metallates into oxometallates, metals oxides, or both.

Certain chemical reactions, such as olefin isomerization reactions for example, may be influenced by the acidity of the composite catalyst. The acidity of the composite catalyst may be controlled by controlling the total number of acidic sites in the composite catalyst. In some embodiments, the number of acidic sites may be proportional to the number of aluminum sites in the composite catalyst, which may be controlled by changing the alumina content of the preformed catalyst material, the alumina content of the catalyst support material, or both. The total number of aluminum sites may also be controlled by changing the weight ratio of the preformed catalyst material to the catalyst support material. In some embodiments, the composite catalyst formed by the aerosol processing methods may have a total acidity of less than or equal to 0.5 millimole/gram (mmol/g), or from 0.01 mmol/g to 0.5 mmol/g, from 0.1 mmol/g to 0.5 mmol/g, from 0.3 mmol/g to 0.5 mmol/g, or from 0.4 mmol/g to 0.5 mmol/g. It will be appreciated that in further embodiments, the composite catalyst may have a total acidity that is less than 0.01 mmol/g or greater than 0.5 mmol/g. In some embodiments in which the composite catalyst comprises a zeolite preformed catalyst material and a metallate catalytically active compound for converting 2-butene to propene, the acidity of the composite catalyst may be sufficient to produce a desired selectivity of propene and reduced production of undesirable by-products, such as aromatics. Increasing acidity may increase the overall butene conversion. However, this increased overall butene conversion may lead to less selectivity and increased production of by-products, such as aromatics for example, which can lead to catalyst coking and deactivation.

The average particle size of the composite catalyst may be controlled by adjusting the concentration of the catalyst support precursors 104 and preformed catalyst materials 105 in the catalyst precursor mixture 108, the type and specification of aerosolizing unit 110, and the reactor configuration. For example, reducing the concentrations of the catalyst support precursors 104, preformed catalyst materials 105, and catalytically active precursors 107 in the catalyst precursor mixture 108 relative to the diluent 106 results in reducing the average particle size of the composite catalyst particles 144 as more of the diluent 106 is available to vaporize from each droplet of the aerosolized catalyst precursor mixture 114. Additionally, different aerosolizing units 110 may produce different size droplets of the aerosolized catalyst precursor mixture 114 during aerosolization, thus, producing different particle sizes of the composite catalyst particles 144. For example, changing the frequency in an ultrasonic nebulizer changes the droplet size of the aerosolized catalyst precursor mixture 114 generated by the ultrasonic nebulizer. Changing the droplet size changes the particle size of the composite catalyst particles 144. Increasing turbulent flow within the aerosolizing unit 110, the heating zone 120, or both may also increase particle size by causing droplets to collide and coalesce together. Similarly, impactors positioned within the aerosolizing unit 110, the heating zone 120, or both may separate larger wet droplets of the aerosolized catalyst precursor mixture 114 and permit only smaller droplets to enter and pass through the heating zone 120. This may result in reducing the average particle size of the composite catalyst particles 144.

In some embodiments, the average particle size of the composite catalyst may be controlled by changing the type and concentrations of the catalyst support precursors in the catalyst precursor mixture. If the catalyst support materials in each droplet react and densify completely to create a solid nonporous catalyst particle, then a mass balance can be performed on the droplet to generate Equation 1, which relates the mean wet droplet diameter ($d_{drop}$) to the dry particle diameter ($d_p$). Equation 1 is provided subsequently in this disclosure.

$$d_p = d_{drop}\left(\frac{MW \times C}{\rho}\right)^{1/3} \qquad \text{EQ. 1}$$

In Equation 1, MW is molecular weight of the formed particle in grams per mol (g/mol), C is the concentration of the catalyst support precursor in moles per cubic centimeter (mol/cm$^3$), and p is the density of the catalyst particle in grams per cubic centimeters (g/cm$^3$). With a calculated wet droplet diameter ($d_{drop}$) of 2.1 μm and a catalyst support precursor comprising a 6.0 wt. % fumed silica precursor suspension, $d_p$ is predicted to be 0.65 μm, assuming complete densification of the fumed silica to reach a density of 2.2 g/cm$^3$. The same calculation for a 6.0 wt. % aluminum (III) nitrate nonahydrate (Al(NO$_3$)$_3$·9H$_2$O) solution results in a $d_p$ of 0.22 μm (completely densified Al$_2$O$_3$ has a density (ρ) of 3.95 g/cm$^3$).

Figure 10A:
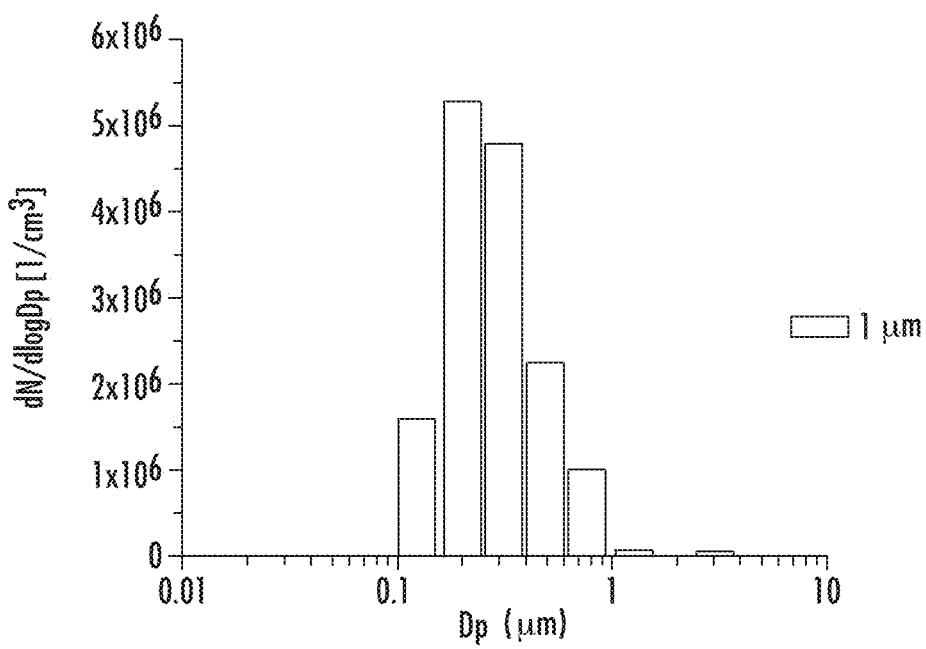
FIG. 10A graphically depicts an average particles size distribution of a catalyst particle produced using aluminum nitrate as the catalyst support precursor, in accordance with one or more embodiments of the present disclosure.
Figure 10B:
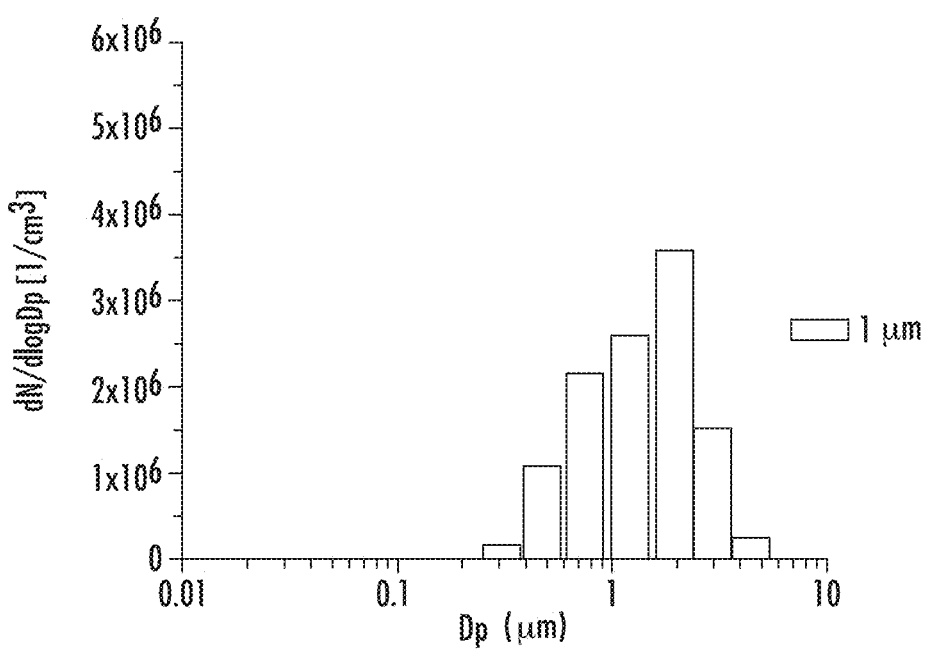
FIG. 10B graphically depicts an average particle size distribution of a catalyst particle produced using fumed silica as the catalyst support precursor, in accordance with one or more embodiments of the present disclosure.

Referring now to FIGS. 10A and 10B, the size distribution of the catalyst particle can be modified by changing the identity of the catalyst support precursor, such as by changing between fumed silica and aluminum nitrate. As shown in FIG. 10A, the mean $d_p$ for catalyst particles made from aluminum nitrate is found to be 0.33 μm. As shown in FIG. 10B, the mean $d_p$ for catalyst particles made from fumed silica is 1.62 μm. The catalyst particles made with the fumed silica have a greater actual particle diameter (average particle size) compared to the predicted diameter calculated from Equation 1. This indicates that the aggregated fumed silica does not densify to the same extent as particles formed from a fully soluble precursor, such as aluminum nitrate.

The average surface area of the composite catalyst may be controlled by adjusting the type and amount of the catalyst support precursors 104 or inclusion of dopants, such as inert constituents, sacrificial constituents, or both, in the catalyst precursor mixture 108. Inert and sacrificial constituents may include polystyrene latex for example. When heated to high temperatures, the polystyrene latex burns off, leaving pores where the polystyrene latex was previously. One having skill in the art will appreciate that other sacrificial continuants may be utilized, which burn off at an elevated temperature to produce a catalyst having an increased average surface area caused by removal of the inert and sacrificial constituents from the composite catalyst. The average surface area of the composite catalyst may also be controlled by adjusting the configuration of the aerosol processing system 100.

The aerosol processing system 100 and the method of making the composite catalyst using the aerosol processing system 100 may result in the catalytically active compound being more dispersed throughout the composite catalyst and less crystalline compared to conventional catalysts made by wet impregnation techniques, such as incipient wetness impregnation. Further, the method of making the composite catalyst using the aerosol processing system 100 does not require a separate calcination step after the composite catalyst particles are formed. Thus, the aerosol processing methods disclosed herein may be more efficient at producing the composite catalysts compared to conventional synthesis methods, such as sol-gel techniques.

In some embodiments, one or more than one of the catalytically active compound precursors 107 may be highly reactive with the preformed catalyst material 105, which may result in at least a portion of the catalytically active compound precursors 107 prematurely reacting with the preformed catalyst material 105 before the composite catalyst particles 144 are fully formed in the heating zone 120. The catalytically active precursor 107 may react with the preformed catalyst material 105 during preparation of the catalyst precursor mixture 108 or during aerosolizing of the catalyst precursor mixture 108. For example, tungsten oxide (catalytically active compound precursor 107) may react with a high alumina content zeolite (preformed catalyst material 105) in the catalyst precursor mixture 108 or in the aerosolized catalyst precursor mixture 114 before the composite catalyst particles 144 are formed. Premature reaction of the catalytically active compound precursor 107 with the preformed catalyst material may reduce the amount of the catalytically active compound ultimately incorporated into the composite catalyst, which may reduce the catalytic activity of the composite catalyst. In some embodiments, premature reaction of the catalytically active compound precursor 107 with the preformed catalyst material 105 may form unwanted byproducts and contaminants that may be deposited in the catalyst support material of the composite catalyst particles 144. These unwanted byproducts and contaminants may decrease the activity of the resultant composite catalyst particles 144. A catalytically active compound precursor 107 that is highly reactive with the preformed catalyst material 105 will be referred to in this disclosure as a reactive catalytically active precursor.

Referring now to FIG. 3, to prevent premature reaction of the reactive catalytically active precursor 116 with the preformed catalyst material 105, the reactive catalytically active precursor 116 may be deposited on the surfaces of the catalyst support material of an intermediate catalyst particle that includes the preformed catalyst material 105 secured within the three dimensional support structure of the catalyst support material.

Referring to FIG. 3, aerosol processing system 300 is depicted for preparing an aerosolized intermediate catalyst particle 118 and depositing the reactive catalytically active precursor 116 onto the surfaces of the aerosolized intermediate catalyst particle 118 to produce composite catalyst particles 344. The composite catalyst particles 344 include the preformed catalyst material 105 secured within the three-dimensional support structure of the catalyst support material with at least one catalytically active compound deposited on the surfaces of the catalyst support material that are accessible to gases and vapors. The aerosol processing system 300 includes the vessel 102, the aerosolizing unit 110 positioned downstream of the vessel 102, a first heating zone 320, a second heating zone 330, and the separator 140.

For aerosol processing system 300, the catalyst support precursor 104, preformed catalyst material 105, and the diluent 106 may be admixed in the vessel 102 to produce the catalyst precursor mixture 108. In some embodiments, the catalyst precursor mixture 108 may include at least one catalytically active compound precursor 107 that is not highly reactive with the preformed catalyst material 105. The catalytically active compound precursor 107 that is not highly reactive with the preformed catalyst material may be admixed with the other components in the vessel 102 to produce the catalyst precursor mixture 108. The catalyst precursor mixture 108 may have any of the compositions or properties previously described in this disclosure, except for lacking the reactive catalytically active precursor 116.

Referring to FIG. 3, the catalyst precursor mixture 108 and the carrier gas 112 may be introduced to the aerosolizing unit 110 and aerosolized to produce an aerosolized catalyst precursor mixture 114 as previously described in this disclosure in relation to the aerosol processing system 100 of FIG. 1. The aerosolized catalyst precursor mixture 114 may be passed to the first heating zone 320, where heat from the first heating zone 320 may vaporize the diluent 106 from the individual droplets of the aerosolized catalyst precursor mixture 114 to produce the aerosolized intermediate catalyst particles 118. Operation of the first heating zone 320 may be similar to operation of heating zone 120 previously described in relation to the aerosol processing system 100 of FIG. 1.

Referring again to FIG. 3, the aerosolized intermediate catalyst particles 118 may include the intermediate catalyst particles entrained in the carrier gas 112. The aerosolized intermediate catalyst particles 118 may be passed to a second heating zone 330 where the reactive catalytically active compound may be deposited onto the surface of the intermediate catalyst particles. The second heating zone 330 may be in tandem with the first heating zone 320, meaning that the second heating zone 330 may be positioned downstream of the first heating zone 320. The aerosolized intermediate catalyst particles 118 may be passed to and through the second heating zone 330 by the carrier gas 112. In some embodiments, the second heating zone 330 may be a second furnace 332, more specifically, a region in a second furnace 332. Alternatively, the second heating zone 330 may comprise another region of the first furnace 322 separate from the first heating zone 320. In some embodiments, the second heating zone 330 may be a second section of a reaction tube that extends through the second furnace 332 or another region of the first furnace 322. In the second heating zone 330, the aerosolized intermediate catalyst particles 118 may be contacted with a reactive catalytically active precursor vapor 336. Although the aerosol processing system 300 and methods are described as having at least a first heating zone 320 and a second heating zone 330, it is contemplated that the aerosol processing system 300 may have more than two heating zones. Additionally, it is contemplated that the first heating zone 320, the second heating zone 330, or both may include multiple temperature regions, which may be independently controlled at different temperatures.

As shown in FIG. 3, in some embodiments, the second heating zone 330 may include a source 334 of the reactive catalytically active precursor vapor 336. In the embodiment shown in FIG. 3, the source 334 of the reactive catalytically active precursor vapor 336 may include a crucible or other open vessel containing the reactive catalytically active precursor 116. Heat from the second heating zone 330 may be transferred to the source 334 and the reactive catalytically active precursor 116 contained within the source 334. The heat from the second heating zone 330 may cause the reactive catalytically active precursor 116 to vaporize to form the reactive catalytically active precursor vapor 336. Alternatively, in some embodiments, the source 334 of the reactive catalytically active precursor vapor 336 may be heated independently of the second heating zone 330, such as by a supplemental heat source controlled independently of the second heating zone 330. The reactive catalytically active precursor 116 may transfer/vaporize into the vapor phase through evaporation, sublimation, reaction, or combinations of these, for example. The reactive catalytically active precursor vapor 336 may distribute throughout the second heating zone 330. In embodiments, the reactive catalytically active precursor 116 may be continuously introduced to the source 334 to maintain continuous production of the reactive catalytically active precursor vapor 336 in the second heating zone 330.

In alternative embodiments, the reactive catalytically active precursor 116 may be vaporized to form the reactive catalytically active precursor vapor 336 in an operation separate from the second heating zone 330, and the reactive catalytically active precursor vapor 336 may be passed into the second heating zone 330 by a supplemental carrier gas. In still other embodiments, the reactive catalytically active precursor vapor 336 may be cooled to form small particles of the reactive catalytically active compound aerosolized in the supplemental carrier gas. These aerosolized particles of the reactive catalytically active compound may then be introduced to the second heating zone 330, where the particles of the reactive catalytically active compound may then be contacted with the aerosolized intermediate catalyst particles 118 to deposit on the surface of the intermediate catalyst particles.

The second heating zone 330 may be maintained at a temperature sufficient to vaporize the reactive catalytically active precursor 116 to generate the reactive catalytically active precursor vapor 336 within the second heating zone 330. In some embodiments, the temperature of the second heating zone 330 may be maintained at a temperature sufficient to maintain a steady state of the reactive catalytically active precursor vapor 336 in the second heating zone 330. In some embodiments, the second heating zone 330 may be maintained at a temperature of from 50° C. to 2000° C. For example, in some embodiments, the second heating zone 330 may be maintained at a temperature of from 50° C. to 1700° C., from 50° C. to 1450° C., from 300° C. to 2000° C., from 300° C. to 1700° C., from 300° C. to 1450° C., from 600° C. to 2000° C., from 600° C. to 1700° C., or from 600° C. to 1450° C. In other embodiments, the second heating zone 330 may be maintained at a temperature of from 600° C. to 1400° C., from 600° C. to 1350° C., from 600° C. to 1300° C., from 600° C. to 1200° C., from 600° C. to 1100° C., from 800° C. to 1450° C., from 800° C. to 1400° C., from 800° C. to 1350° C., from 800° C. to 1300° C., from 800° C. to 1200° C., from 800° C. to 1100° C., from 1000° C. to 1450° C., from 1000° C. to 1400° C., from 1000° C. to 1350° C., from 1000° C. to 1300° C., from 1000° C. to 1200° C., from 1100° C. to 1450° C., or from 1200° C. to 1450° C. In embodiments, the temperature of the second heating zone 330 may be controlled to control the vaporization rate of the reactive catalytically active precursor 116.

In some embodiments, the second heating zone 330 may be operated at ambient pressure. Alternatively, the second heating zone 330 may also be operated at positive pressure or under a vacuum. A vapor pressure of the reactive catalytically active precursor vapor 336 in the second heating zone 330 may be controlled by controlling the temperature of the second heating zone 330, the temperature of the source 334 of the reactive catalytically active precursor vapor 336, or both. The vapor pressure of the reactive catalytically active precursor vapor 336 may also be controlled by controlling the flow rate of carrier gas 112 through the second heating zone 330.

In embodiments, the residence time of the aerosolized intermediate catalyst particles 118 in the second heating zone 330 may be from 0.1 seconds to 10 seconds. In other embodiments, the residence time of the catalyst support particles 114 in the second heating zone 330 may be from 0.1 seconds to 9 seconds, from 0.1 seconds to 8 seconds, 0.1 second to 6 seconds, from 0.1 second to 4 seconds, from 0.5 seconds to 10 second, from 0.5 second to 9 seconds, from 0.5 seconds to 8 seconds, from 0.5 seconds to 6 seconds, from 0.1 second to 0.4 seconds, from 1 second to 10 seconds, from 1 second to 9 seconds, from 1 seconds to 8 second, from 1 second to 6 seconds, from 1 second to 4 seconds, from 2 seconds to 10 seconds, from 2 seconds to 9 seconds, from 2 seconds to 8 seconds, from 2 seconds to 6 seconds, or from 2 seconds to 4 seconds.

The aerosolized intermediate catalyst particles 118 may be contacted with the reactive catalytically active precursor vapor 336 in the second heating zone 330. Stream 326 may be passed out of the second heating zone 330. Stream 326 may include the aerosolized intermediate catalyst particles 118, the reactive catalytically active precursor vapor 336, the carrier gas 112, and any other volatile constituents of the catalyst precursor mixture 108 vaporized in the first heating zone 320 and the second heating zone 330. Upon exiting the second heating zone 330, the reactive catalytically active precursor vapor 336 and the aerosolized intermediate catalyst particles 118 may be cooled. In some embodiments, the aerosolized intermediate catalyst particles 118 and the reactive catalytically active precursor vapor 336 may be cooled at a controlled rate to a temperature of less than 120° C., such as a temperature from 20° C. to 120° C. A desired cooling rate of the aerosolized intermediate catalyst particles 118 and reactive catalytically active precursor vapor 336 may be achieved by modifying the residence time in the second heating zone 330 or by changing the distance between the second heating zone 330 and the separator 140. Additionally, the cooling rate of the aerosolized intermediate catalyst particles 118 and the reactive catalytically active precursor vapor 336 may be controlled using fans or heat exchangers or by changing the insulation materials. Further, the cooling rate of the aerosolized intermediate catalyst particles 118 and the reactive catalytically active precursor vapor 336 may be controlled by controlling a temperature of the separator 140.

As the reactive catalytically active precursor vapor 336 cools, the reactive catalytically active precursor vapor 336 may condense. The reactive catalytically active precursor vapor 336 may condense directly onto the surfaces of the intermediate catalyst particles, such as onto the catalyst support material. Additionally, the reactive catalytically active precursor vapor 336 may condense onto reactive catalytically active compound previously condensed on the surface of the intermediate catalyst particles. In some embodiments, the reactive catalytically active precursor vapor 336 may condense on the outermost surfaces of the intermediate catalyst particles and on surfaces of the intermediate catalyst particles that are accessible to gases and vapors, such as porous regions of the catalyst support material of the intermediate catalyst particles. Alternatively or additionally, the reactive catalytically active precursor vapor 336 may condense onto itself (homogeneous nucleation) to create clusters or particles of the reactive catalytically active compound that may then diffuse to the intermediate catalyst particles and deposit onto the surfaces of the intermediate catalyst particles. The clusters or particles of the reactive catalytically active compound may deposit onto the outermost surfaces of the intermediate catalyst particles and on surfaces of the intermediate catalyst particles that are accessible to gases and vapors.

Deposition of the reactive catalytically active compound may result in formation of the composite catalyst particles 344 that includes the preformed catalyst material encased in the catalyst support material and individual atoms, molecules, clusters, or particles of the reactive catalytically active compound deposited on the surfaces of the composite catalyst that are accessible to gases and vapors. The composite catalyst may also include at least one catalytically active material distributed throughout the catalyst support material. Thus, in some embodiments, the composite catalyst may have one catalytically active compound distributed throughout the catalyst support material and another reactive catalytically active compound deposited on the surfaces of the composite catalyst that are accessible to gases and vapors. In these embodiments, the interior portions of the catalyst support material and preformed catalyst material of the composite catalyst may be substantially free of the reactive catalytically active compound. As used in this disclosure, the term "substantially free" of a component means less than 0.1 wt. % of that component in a particular portion of a catalyst, stream, or reaction zone. For example, the interior portions of the composite catalyst may have less than 0.1 wt. % reactive catalytically active compound, based on the total weight of the composite catalyst. The interior portions of the composite catalyst refer to the portions of the catalyst support material and preformed catalyst material that are inaccessible to gases and vapors. For example, the interior of the composite catalyst may include the solid portions of the catalyst support material and preformed catalyst material and the internal pores of the catalyst support material and preformed catalyst material that are not in fluid communication with the outer surface of the composite catalyst particle.

In some embodiments, the aerosol processing system 300 may also include the separator 140 for separating the composite catalyst particles 344 from the gases 346 and collecting the composite catalyst particles 344. The gases 346 in which the composite catalyst particles 344 may include the carrier gas 112, uncondensed reactive catalytically active precursor vapor 336, or other volatile constituents of the catalyst precursor mixture 108, such as vaporized diluent for example. The stream 326, which includes the gases 346 and the composite catalyst particles 344 entrained in the gases 346, may be passed from second heating zone 330 the separator 140. The method of synthesizing the composite catalyst may include separating the composite catalyst particles 344 from the gases 346 and collecting the composite catalyst particles 344. In some embodiments, the gases 346 exiting the separator 140 may be further processed to recover residual constituents of the process, such as reactive catalytically active compound precursor vapors 336, organic solvents from the catalyst precursor mixture 108, other reactants or contaminants, or combinations of these.

The amount of the reactive catalytically active compound deposited onto the surfaces of the intermediate catalyst particles may be controlled by controlling the concentrations of the catalyst support precursor 104 and preformed catalyst material 105 in the catalyst precursor mixture 108. The amount of reactive catalytically active compound deposited on the surfaces of the intermediate catalyst particles may also be controlled through the selection of and temperature of the reactive catalytically active precursor 116 in the second heating zone 330 such as by controlling the temperature of the second heating zone 330, the temperature of the source 334 of the reactive catalytically active precursor vapor 336, or both, which may influence the vaporization rate of the reactive catalytically active precursor 116. The amount of reactive catalytically active compound deposited onto the surfaces of the intermediate catalyst particles may also be controlled by controlling the flowrate of the aerosolized intermediate catalyst particles 118 through the second heating zone 330, the concentrations of the catalyst support precursor 104 and preformed catalyst material 105 in the catalyst precursor mixture 108, the particle size of the aerosolized intermediate catalyst particles 118, the temperature of the aerosolized intermediate catalyst particles 118, the final temperature of the aerosol at the separator 140, the concentration of the intermediate catalyst particles in the carrier gas 112, or combinations of these.

In one example implementation, the aerosol process methods previously discussed may be used to synthesize a multi-functional composite catalyst for producing olefins from a hydrocarbon feed stream through a combination of isomerization, metathesis, and cracking reactions. The multi-functional composite catalyst may exhibit isomerization, metathesis, and cracking catalytic activity and may be useful in a metathesis process for producing propene from a hydrocarbon stream comprising butene. For example, the multi-functional composite catalyst may comprise a zeolite, such as an MFI structured zeolite, for the preformed catalyst material. The catalyst support material of the multi-functional composite catalyst may include fumed silica or fumed silica/alumina. Further, the multi-functional composite catalyst may include tungsten oxide ($WO_3$) or other metal oxide as the catalytically active compound. The zeolite may provide catalytic activity for cracking, the tungsten oxide or other metal oxide may provide catalytic activity for metathesis reactions, and the fumed silica or fumed silica/alumina may provide catalytic activity for isomerization.

Referring to Reaction 1 (RXN 1), which is provided subsequently in the present disclosure, isomerization of 2-butenes (which may include isomers cis-2-butene, trans-2-butene, or both) to 1-butene, and vice versa, is an equilibrium reaction as denoted by the bi-directional arrows with single heads. The isomerization may be achieved with the isomerization portion of the multi-functional composite catalyst. The "isomerization portion" of the multi-functional composite catalyst, as used in this disclosure, refers to the preformed catalyst material, catalyst support material, or catalytically active compound that exhibits catalytic activity for isomerizati on of alkenes, including, for example, isomerization of 2-butenes to 1-butene.

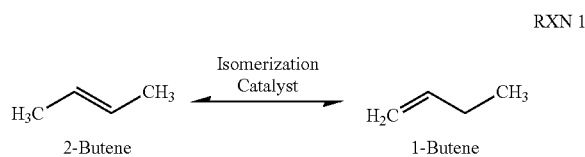

RXN 1

Cross-metathesis may be achieved as shown in Reaction 2 (RXN 2), which is provided subsequently in the present disclosure, with the metathesis portion of the multi-functional composite catalyst. As used in this disclosure, "cross-metathesis" refers to an organic reaction that involves the redistribution of fragments of alkenes by the scission and regeneration of carbon-carbon double bonds. In the case of 2-butenes and 1-butene, the redistribution of these carbon-carbon double bonds through metathesis produces propene and $C_5$-$C_6$ olefins. The "metathesis portion" of the multi-functional composite catalyst, as used in this disclosure, refers to the preformed catalyst material, catalyst support material, or catalytically active compound that exhibits catalytic activity for conducting a metathesis reaction of alkenes to form other alkenes. For example, in some embodiments, the tungsten oxide included in the multi-functional composite catalyst as one catalytically active compound may be the metathesis portion of the multi-functional composite catalyst. The metathesis portion of the multi-functional composite catalyst may also isomerize 2-butenes to 1-butene through a "self-metathesis" reaction mechanism.

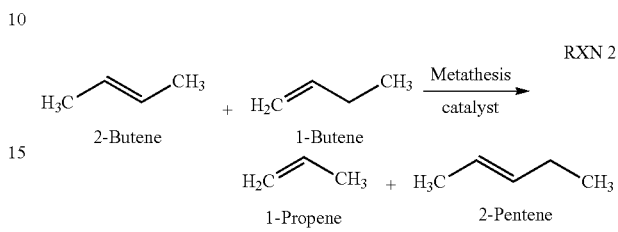

RXN 2

Further, as shown in the following Reaction 3 (RXN 3), which is provided subsequently in this disclosure, "cracking" refers to the catalytic conversion of $C_4$-$C_6$ alkenes to propene and other alkanes, alkenes, or alkanes and alkenes, for example, $C_1$-$C_2$ alkenes.

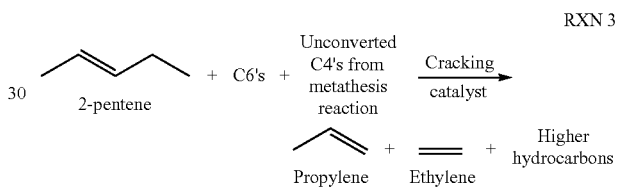

RXN 3

Referring to RXN 1-RXN3, the isomerization, metathesis, and cracking reactions are not limited to these reactants and products; however, RXN 1-RXN 3 provide a simplified illustration of the reaction methodology.

As shown in RXN 1, isomerization of 2-butene is an equilibrium reaction between 2-butene and 1-butene. The isomerization reaction of RXN 1 may be catalyzed by the fumed silica, alumina, fumed alumina, or combination of both in the catalyst support material of the multi-functional composite catalyst. As shown in RXN 2, metathesis reactions may take place between two alkenes. The groups bonded to the carbon atoms of the carbon-carbon double bond may be exchanged between the molecules to produce two new alkenes with the exchanged groups. The metathesis reaction of RXN 2 may be catalyzed by one or more than one of the catalytically active compounds, such as an oxometallate or metal oxide, supported by the catalyst support material of the multi-functional composite catalyst. The specific catalytically active compound that is selected as the catalyst for the olefin metathesis reaction may generally determine whether a cis-isomer or trans-isomer is formed, as the formation of a cis- or trans-isomer may be a function at least partially of the coordination of the olefin molecules with the catalyst, as may be the steric influences of the substituents on the carbon-carbon double bond of the newly formed molecule. In some embodiments, the catalytically active compound for catalyzing the olefin metathesis reaction may be tungsten or tungsten oxide. The cracking reactions represented by RXN 3 may be catalyzed by the preformed catalyst material. In some embodiments, the preformed catalyst material may be a MFI structured zeolite catalyst. In some embodiments, the composite catalyst may enable producing propene from 2-butene without the addition of ethylene as a reactant to the reactions system.

EXAMPLES

The following examples illustrate the preparation of various multi-functional composite catalysts for producing propene from 2-butene through a combination of isomerization, metathesis, and cracking reactions. These multi-functional composite catalysts were then used to produce propene from a stream of 2-butene and nitrogen in a fixed bed reactor operated at 580° C.

Example 1

Preparation of Composite Catalysts Including and MFI Structured Zeolite and a Weight Ratio of Zeolite to Other Constituents of 1:1

For Example 1, a composite catalyst was synthesized using a MFI structured zeolite with weight ratio of silica to alumina of 1012:1 as the preformed catalyst material, fumed silica as the catalyst support material, and ammonium metatungstate hydrate as the catalytically active compound precursor. The composite catalyst of Example 1 was synthesized using an aerosol processing system as previously described in this disclosure. A catalyst precursor mixture was prepared by adding 1.09 grams of fumed silica, 0.187 grams of ammonium metatungstate hydrate, and 1.2 grams of zeolite to 40 grams of deionized ultrapure water. Ultrapure water refers to water subjected to treatments to remove organic compounds and dissolved gases to meet strict water purity standards such as those provided in American Society for Testing and Materials (ASTM) standard D5127. The fumed silica was AEROSIL® 380 fumed silica marketed by Evonik, and the ammonium metatungstate hydrate was obtained from Strem Chemicals, Inc. The zeolite was an MFI structured zeolite having a weight ratio of silica to alumina of about 1012:1. The catalyst precursor mixture exhibited a solids content of about 6 wt. %. The weight ratio of the zeolite to the fumed silica and ammonium metatungstate hydrate was 1:1. The catalyst precursor mixture was mixed and the ultrasonicated for 10 minutes.

The aerosolizing unit used to aerosolize the catalyst precursor mixture was a Buchi Mini Spray Dryer model B-290 with a two-fluid nozzle with a 0.5 mm nozzle tip, a 1.4 millimeter (mm) nozzle cap, and a 0.3 mm needle (for nozzle cleaning). The spray dryer was allowed to equilibrate for 15 minutes with air at 200° C. Exit temperature of the air during equilibration was 120° C. Once the spray dryer was equilibrated, the catalyst precursor mixture was introduced to the spray dryer and aerosolized into a fine mist of micrometer sized droplets. The air introduced to the spray dryer nozzle was at an incoming temperature of 200° C. and a flow rate of about 2.3 Liters per minute (L/min). The liquid feed rate of the liquid catalyst precursor mixture to the spray dryer was 15 milliliters per minute (mL/min). The temperature at the exit of the nozzle was from 105° C. to 110° C. The composite catalyst particles of Example 1 were analyzed for elemental composition using Inductively Coupled Plasma Mass Spectroscopy (ICP-MS). The composite catalyst particles of Example 1 were found to include 6.06 wt. % tungsten, 40.3 wt. % silicon, and 0.365 wt. % aluminum.

Example 2

Preparation of Composite Catalysts Including MFI Structured Zeolite and a Weight Ratio of MFI-400 Zeolite to Other Constituents of 1:10

For Example 2, a composite catalyst was synthesized using a MFI structured zeolite with weight ratio of silica to alumina of 206:1 as the preformed catalyst material, fumed silica as the catalyst support material, and ammonium metatungstate hydrate as the catalytically active compound precursor. A catalyst precursor mixture was prepared by adding 5.45 grams of fumed silica, 0.933 grams of ammonium metatungstate hydrate, and 0.667 grams of zeolite to 111.11 grams of deionized ultrapure water. The fumed silica was AEROSIL® 380 fumed silica marketed by Evonik, and the ammonium metatungstate hydrate was obtained from Strem Chemicals, Inc. The zeolite was an MFI structured zeolite having a weight ratio of silica to alumina of about 206:1. The catalyst precursor mixture exhibited a solids content of about 6 wt. %. The weight ratio of the zeolite to the fumed silica and ammonium metatungstate hydrate was 1:10. The catalyst precursor mixture was mixed and the ultrasonicated for 10 minutes.

The catalyst precursor mixture was aerosolized and passed through the spray dryer as previously described in Example 1 to produce the composite catalyst particles of Example 2. The composite catalyst particles of Example 2 were then dried in a drying oven at 110° C. overnight and then calcined under a flow of air at 550° C. for 5 hours. The composite catalyst particles of Example 2 were analyzed for elemental composition using Inductively Coupled Plasma Mass Spectroscopy (ICP-MS). The composite catalyst particles of Example 2 were found to include 9.78 wt. % tungsten, 36.8 wt. % silicon, and 0.022 wt. % aluminum.

Examples 3A and 3B

Preparation of Composite Catalysts Including ZSM-5 Zeolite from ACS and a Weight Ratio of Zeolite to Other Constituents of 1:10

For Examples 3A and 3B, two composite catalysts were synthesized using a MFI structured zeolite with weight ratio of silica to alumina of 371:1 as the preformed catalyst material, fumed silica as the catalyst support material, and ammonium metatungstate hydrate as the catalytically active compound precursor. For Example 3A, the catalyst was produced using a spray dryer. For Example 3A, a catalyst precursor mixture was prepared by adding 5.45 grams of fumed silica, 0.933 grams of ammonium metatungstate hydrate, and 0.667 grams of zeolite to 111.11 grams of deionized ultrapure water. The fumed silica was AEROSIL® 380 fumed silica marketed by Evonik, and the ammonium metatungstate hydrate was obtained from Strem Chemicals, Inc. The zeolite was H-ZSM-5 zeolite P-371 obtained from ACS Material. The H-ZSM-5 zeolite from ACS Material is a MFI structured zeolite having a weight ratio of silica to alumina of about 371:1. The catalyst precursor mixture exhibited a solids content of about 6 wt. %. The weight ratio of the zeolite to the fumed silica and ammonium metatungstate hydrate was 1:10. The catalyst precursor mixture was mixed and the ultrasonicated for 10 minutes.

For Example 3A, the catalyst precursor mixture was aerosolized and passed through the spray dryers as previously described in Example 1 to produce the composite catalyst particles of Example 3A. The composite catalyst particles of Example 3A were then dried in a drying oven at 110° C. overnight and then calcined under a flow of air at 550° C. for 5 hours. The composite catalyst particles of Example 3A were analyzed for elemental composition using Inductively Coupled Plasma Mass Spectroscopy (ICP-MS). The composite particles of Example 3A were found to include 9.43 wt. % tungsten, 38.5 wt. % silicon, and 0.024 wt. % aluminum.

For Example 3B, the catalyst was synthesized using an aerosol processing system. For Example 3B, a catalyst precursor mixture was prepared by adding 5.49 grams of fumed silica, 1.03 grams of ammonium metatungstate hydrate, and 0.55 grams of zeolite to 150 grams of deionized ultrapure water. The fumed silica was AEROSIL® 380 fumed silica marketed by Evonik, and the ammonium metatungstate hydrate was obtained from Strem Chemicals, Inc. The zeolite was H-ZSM-5 zeolite P-371 obtained from ACS Material. The H-ZSM-5 zeolite from ACS Material is a MFI structured zeolite having a weight ratio of silica to alumina of about 371:1. The catalyst precursor mixture exhibited a solids content of about 6 wt. %. The weight ratio of the zeolite to the fumed silica and ammonium metatungstate hydrate was 1:10. The catalyst precursor mixture was mixed and the ultrasonicated for 10 minutes.

In Example 3B, the aerosol was introduced into a 0.5 inch quartz tube using an ultrasonic transducer, which was passed through a tube furnace maintained at a temperature of 600° C. to produce the composite catalyst particles of Example 1. The carrier gas was a particle-free, oil-free air, and the air flow through the tube furnace was set to 2.25 L/min. The composite catalyst particles of Example 3B were then collected in a ceramic filter particle collector positioned downstream of the tube furnace. The composite catalyst particles of Example 3B were then dried in a drying oven at 110° C. overnight and then calcined under a flow of air at 550° C. for 5 hours. The composite catalyst particles of Example 3B were analyzed for elemental composition using ICP-MS. The composite particles of Example 3B were found to include 11.0 wt. % tungsten and 0.0794 wt. % aluminum. The silicon content of the composite particles of Example 3B was not measured.

Example 4

Preparation of Composite Catalysts Including ZSM-5 Zeolite from ACS and a Weight Ratio of Zeolite to Other Constituents of 1:20

For Example 4, a composite catalyst was synthesized using a MFI structured zeolite with weight ratio of silica to alumina of 371:1 as the preformed catalyst material, fumed silica as the catalyst support material, and ammonium metatungstate hydrate as the catalytically active compound precursor. The amount of zeolite relative to the other constituents was less in Example 4 compared to Example 3. A catalyst precursor mixture was prepared by adding 5.45 grams of fumed silica, 0.933 grams of ammonium metatungstate hydrate, and 0.316 grams of zeolite to 105.56 grams of deionized ultrapure water. The fumed silica was AEROSIL® 380 fumed silica marketed by Evonik, and the ammonium metatungstate hydrate was obtained from Strem Chemicals, Inc. The zeolite was H-ZSM-5 zeolite P-371 obtained from ACS Material. The H-ZSM-5 zeolite from ACS Material is a MFI structured zeolite having a weight ratio of silica to alumina of about 371:1. The catalyst precursor mixture exhibited a solids content of about 6 wt. %. The weight ratio of the zeolite to the fumed silica and ammonium metatungstate hydrate was 1:20. The catalyst precursor mixture was mixed and the ultrasonicated for 10 minutes.

The catalyst precursor mixture was aerosolized and passed through the spray dryer as previously described in Example 1 to produce the composite catalyst particles of Example 4. The composite catalyst particles of Example 4 were then dried in a drying oven at 110° C. overnight and then calcined under a flow of air at 550° C. for 5 hours. The composite catalyst particles of Example 4 were analyzed for elemental composition using Inductively Coupled Plasma Mass Spectroscopy (ICP-MS). The composite particles of Example 4 were found to include 9.71 wt. % tungsten, 38.6 wt. % silicon, and less than 0.0218 wt. % aluminum.

Comparative Example 5

Particulate Catalyst Mixture of a MFI Structured Catalyst and a Metathesis Catalyst For Comparative Example 5, a physical catalyst mixture of two separate particulate solid catalysts was prepared. The catalyst mixture included equal parts by weight of an MFI-2000 zeolite catalyst and a metathesis catalyst. The MFI-2000 zeolite catalyst had a weight ratio of silica to alumina of 1012:1.

The metathesis catalyst in Comparative Example 5 was synthesized from silica and ammonium metatungstate using the aerosol processing system of Example 1. A catalyst precursor mixture was prepared by mixing 5.45 grams of fumed silica with 0.933 grams of ammonium metatungstate hydrate and then adding 100 grams of water. The fumed silica was AEROSIL® 380 fumed silica marketed by Evonik, and the ammonium metatungstate hydrate was obtained from Strem Chemicals, Inc. No zeolite was added to the catalyst precursor mixture. The catalyst precursor mixture was then mixed and ultrasonicated.

The aerosolizing unit used to aerosolize the catalyst precursor mixture was a Buchi Mini Spray Dryer model B-290 with a two-fluid nozzle with a 0.5 mm nozzle tip, a 1.4 millimeter (mm) nozzle cap, and a 0.3 mm needle (for nozzle cleaning). The spray dryer was allowed to equilibrate for 15 minutes with air at 200° C. The exit temperature of the air during equilibration was 120° C. Once the spray dryer was equilibrated, the catalyst precursor mixture was introduced to the spray dryer and aerosolized into a fine mist of micrometer sized droplets. The air introduced to the spray dryer nozzle was at an incoming temperature of 200° C. and a flow rate of less than 10 Liters per minute (L/min). The liquid feed rate of the liquid catalyst precursor mixture to the spray dryer was 7 milliliters per minute (mL/min). The temperature at the exit of the nozzle was from 102° C. to 120° C.

The metathesis catalyst particles were then physically mixed with an equal weight of the MFI-2000 zeolite catalyst to produce the physical catalyst mixture of Comparative Example 5.

Comparative Example 6

Metathesis Catalyst Prepared By Incipient Wetness Impregnation

For Comparative Example 6, a metathesis catalyst made by conventional incipient wetness impregnation techniques was provided as a comparison to the composite catalysts of Examples 1-3. The metathesis catalyst of comparative Example 6 included a commercial silica support impregnated with a solution of ammonium metatungstate hydrate (AMT) using incipient wetness impregnation techniques. The commercial silica support was CARiACT Q-10 silica support obtained from Fuji Silysia Chemical. A solution of 2.32 g of AMT dissolved in 30 mL of deionized water was prepared. Next, 1.00 g of the commercial silica support was mixed with 1.83 mL of the AMT solution and 2.51 mL of deionized water to achieve a target 10 wt. % tungsten loading in the resulting metathesis catalysts. The suspension was stirred and heated at 80° C. for three hours to evaporate the water. The resulting powder was then heated at 5° C./min to reach the calcination temperature of 550° C., which was held for 5 hrs under static air.

Comparative Example 7

Metathesis Catalyst Prepared by an Aerosol Process

For Comparative Example 7, a metathesis catalyst was prepared using the aerosol processing system described in Example 1. First, an initial precursor mixture was prepared by adding 27.23 grams of fumed silica and 4.681 grams of ammonium metatungstate hydrate to 500 grams of deionized ultrapure water. The fumed silica was AEROSIL® 380 fumed silica marketed by Evonik, and the ammonium metatungstate hydrate was obtained from Strem Chemicals, Inc. The initial precursor mixture had a solids content of 6 wt. % solids. 200 grams of the initial precursor mixture was then diluted with an additional 66.6 grams of deionized ultrapure water to dilute the precursor mixture to form a diluted precursor mixture having a solids concentration of 4.5 wt. % solids.

The diluted precursor mixture was aerosolized using the aerosolizing unit (described in 3b). The air flow rate was 100 L/min and the feed rate of the diluted precursor mixture to the spray dryer was 0.9 mL/min. The aerosolized precursor mixture was passed through the tube furnace, which was maintained at a temperature of 600° C. The process was operated for a period of 3 hours. The solid metathesis catalyst particles were collected with the filter. The metathesis catalyst particles were then dried at 110° C. overnight and then calcined at a temperature of 550° C. for 6 hours. The resulting metathesis catalyst of Comparative Example 7 consisted of a fumed silica catalyst support having tungsten oxide distributed throughout the fumed silica catalyst support. The metathesis catalyst of Comparative Example 7 did not have a zeolite or other preformed catalyst material encased in the fumed silica catalyst support.

Example 8

Evaluation of the BET Surface Area and Pore Volume of the Composite Catalysts of Examples 1 and 2 and the Metathesis Catalyst of Comparative Example 7

In Example 8, the composite catalysts of Examples 1 and 2, the metathesis catalyst of Comparative Example 7, and the preformed catalyst materials used to make the composite catalysts of Examples 1 and 2 were evaluated for BET surface area and cumulative pore volume. The results for the BET surface area and cumulative pore volumes are shown in Table 1 provided subsequently.

TABLE 1

BET Surface Area and Cumulative Pore Volume for Composite Catalysts of Examples 1 and 2 and Metathesis Catalyst of Comparative Example 7

| Material | BET Surface Area (m$^2$/g) | Cumulative Pore Volume (cm$^3$/g) |
|---|---|---|
| Composite Catalyst of Example 1 | 303 | 0.762 |
| Composite Catalyst of Example 2 | 275 | 0.990 |
| Metathesis Catalyst of Comp. Ex. 7 | 226 | 0.664 |
| MFI Zeolite (silica:alumina of 1012:1) | 487 | 0.389 |
| MFI Zeolite (silica:alumina of 206:1) | 434 | 0.364 |

As shown in Table 1, the cumulative pore volumes for the composite catalysts of Examples 1 and 2 were greater than the cumulative pore volume of the metathesis catalyst of Comparative Example 7 and greater than the cumulative pore volumes of the MFI zeolites used as the preformed catalyst material in the composite catalysts of Examples 1 and 2. AEROSIL® 380 fumed silica was used in the synthesis of the metathesis catalyst of Comparative Example 7, and was also used as the catalyst support precursor for the composite catalysts of Examples 1 and 2. The composite catalysts of Example 1 and 2 also included the MFI structured zeolites as the preformed catalyst materials. The MFI zeolite materials exhibited an even lesser cumulative pore volume than the metathesis catalyst of Comparative Example 7. It was expected that the combination of the MFI zeolite materials with the fumed silica catalyst support precursor would reduce the cumulative pore volume of the composite catalyst of Examples 1 and 2 compared to the metathesis catalyst of Comparative Example 7. However, the cumulative pore volume of the composite catalyst of Examples 1 and 2 was unexpectedly greater than the cumulative pore volume of the metathesis catalyst of Comparative Example 7 as well as each of the MFI zeolite materials.

Example 9

Evaluation of the Performance of Composite Catalysts of Examples 1-3 and the Catalysts of Comparative Examples 5-7 for Producing Propene from 2-Butene The metathesis catalysts of Examples 1-3 and Comparative Examples 5-7 were evaluated for their performance in metathesizing 2-butene to propene. The performance of each of the example composite catalysts and comparative catalysts were tested in a fixed bed reactor for conversion of a stream of 2-butene to propene. Referring to FIG. 4, the fixed-bed flow reactor system 400 included a tube furnace reactor 402 and a quartz reaction tube 404 extending through the tube furnace reactor 402 and having an inlet 406 and an outlet 408. Each catalyst or catalyst mixture was placed in the reaction tube 404 in a catalyst bed 410 disposed between layers of quartz wool 412. The inlet 406 of the reaction tube 404 was fluidly coupled to a butene stream inlet 414 and a nitrogen inlet 416. The outlet 408 of the reaction tube 404 was fluidly coupled to a gas chromatograph with a flame ionization detector 420 (GC/FID system) so that the product stream 418 passed out of the reaction tube 404 and directly into the GC/FID system 420.

Each composite catalyst, catalyst mixture, and metathesis catalyst was tested sequentially to provide performance data for each. 100 milligrams of each composite catalyst, catalyst mixture, and metathesis catalyst was charged to the catalyst bed 410 portion of the reaction tube 404. Each catalyst was first activated at 580° C. under nitrogen flow at 0.005 liters/minute (L/min) for 30 minutes. At the desired reaction temperature (580° C.), a feed stream of 2-butene was introduced to the nitrogen flow. The reaction was performed at 580° C. and at a gas hourly space velocity of 900 per hour (h$^{-1}$), using nitrogen as a diluent. The feed stream had 10 wt. % 2-butene based on the total mass flow rate of the feed stream. The product stream 418 exiting the fixed bed flow reactor 400 was passed to the GC/FID system 420 for analysis of the product stream 418. The percentage of propene selectivity, 2-butene conversion, absolute propene yield, absolute ethylene yield, and yield of C$_6$+ compounds for the composite catalysts of Examples 1-3 and the catalysts of Comparative Examples 5-7 are provided subsequently in Table 2.

Figure 6:
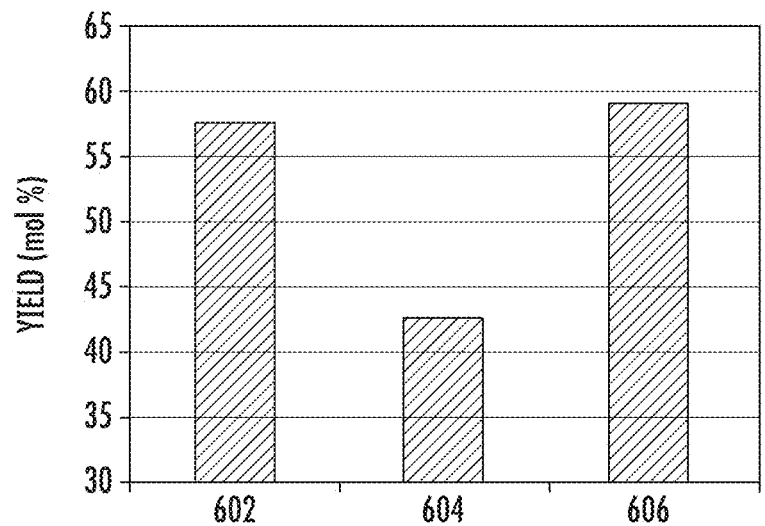
FIG. 6 graphically depicts the total yield of propene and ethylene (y-axis) obtained from the reaction system of FIG. 4 for converting 2-butene to propene using the composite catalyst of Example 1, the physical mixture of catalysts in Comparative Example 5 and the metathesis catalyst of Comparative Example 6 (x-axis), in accordance with one or more embodiments of the present disclosure.

Example 6. The MFI zeolite in the physical mixture was an MFI-2000 zeolite having a weight ratio of silica to alumina of 1012:1. As shown graphically in FIG. 6, the combined propene and ethylene yield for the composite catalyst of Example 1 (602) (57.73%) was 35% greater than the combined propene and ethylene yield for the metathesis catalyst of Comparative Example 6 (604) (42.76%). As shown in FIG. 6, the combined propene and ethylene yield for the composite catalyst of Example 1 (602) (57.73%) was comparable to the combined propene and ethylene yield for the physical catalyst mixture of the metathesis catalyst of Comparative Example 6 and the MFI zeolite (606) (59.02%).

Figure 11:
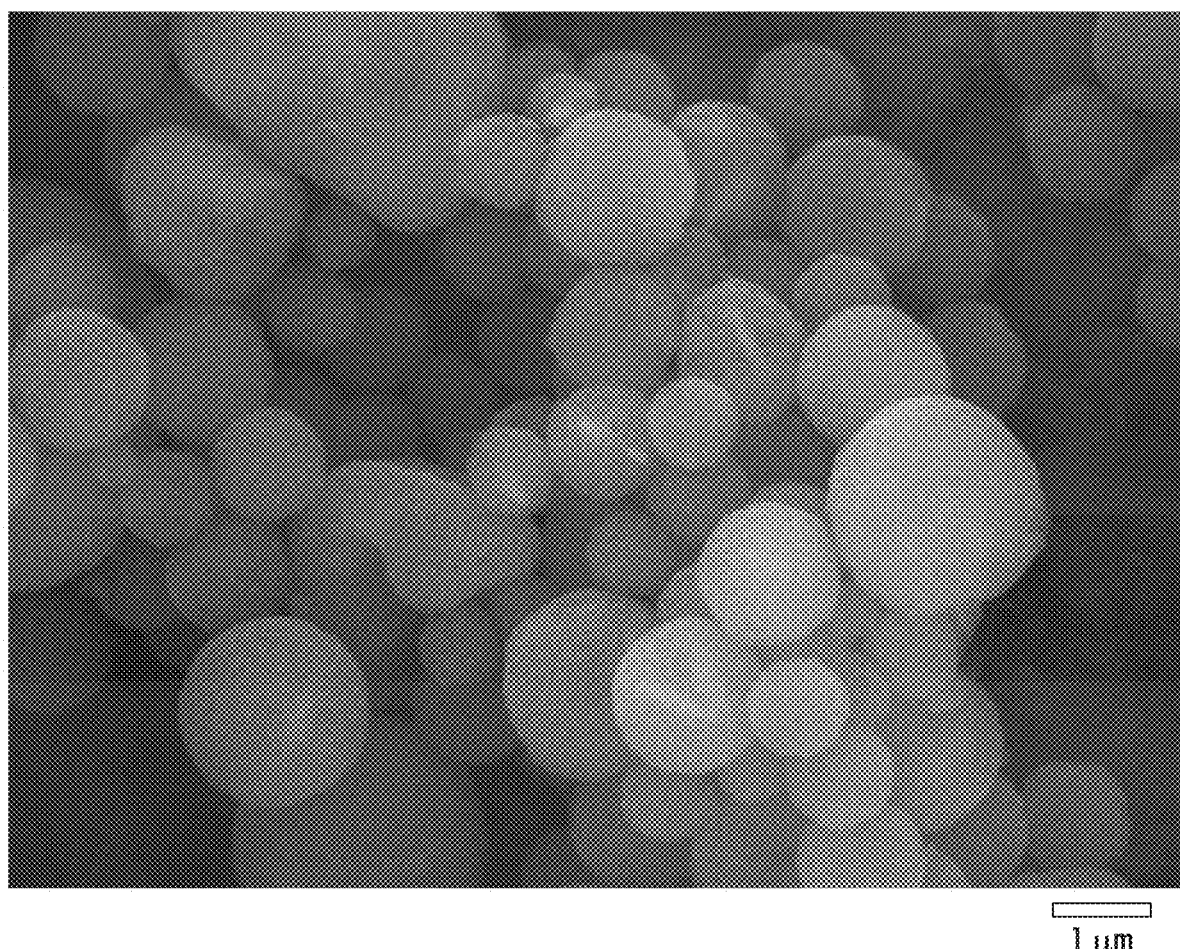
FIG. 11 provides an SEM photograph of the composite catalyst, in accordance with one or more embodiments of the present disclosure.

FIG. 11 provides an SEM photograph of the composite catalyst of the present disclosure, the composite catalyst

TABLE 2

Performance of composite catalysts of Examples 1-3 and catalysts of Comparative Examples 5-7 for conversion of 2-Butene to Propene

| Ex. | Ref. No. in FIG. 5 | Propene Selectivity (%) | 2-Butene Conversion (%) | Absolute Propene Yield (%) | Absolute Ethylene Yield (%) | Ethylene + Propene Yield (%) | C$_6$+ Yield (%) |
|---|---|---|---|---|---|---|---|
| Ex. 1 | 520 | 40.10 | 90.72 | 36.37 | 21.36 | 57.73 | 10.46 |
| Ex. 2 | 530 | 36.93 | 92.41 | 34.13 | 23.29 | 57.42 | 16.15 |
| Ex. 3A | 550 | 36.00 | 90.28 | 32.47 | 17.43 | 49.90 | 16.44 |
| Comp. 5 | 510 | 43.16 | 90.16 | 38.91 | 22.54 | 61.46 | 7.60 |
| Comp. 6 | 540 | 41.67 | 80.70 | 33.63 | 9.13 | 42.76 | 12.37 |
| Comp. 7 | 560 | 38.33 | 83.66 | 32.05 | 10.10 | 42.15 | 15.95 |

Figure 5:
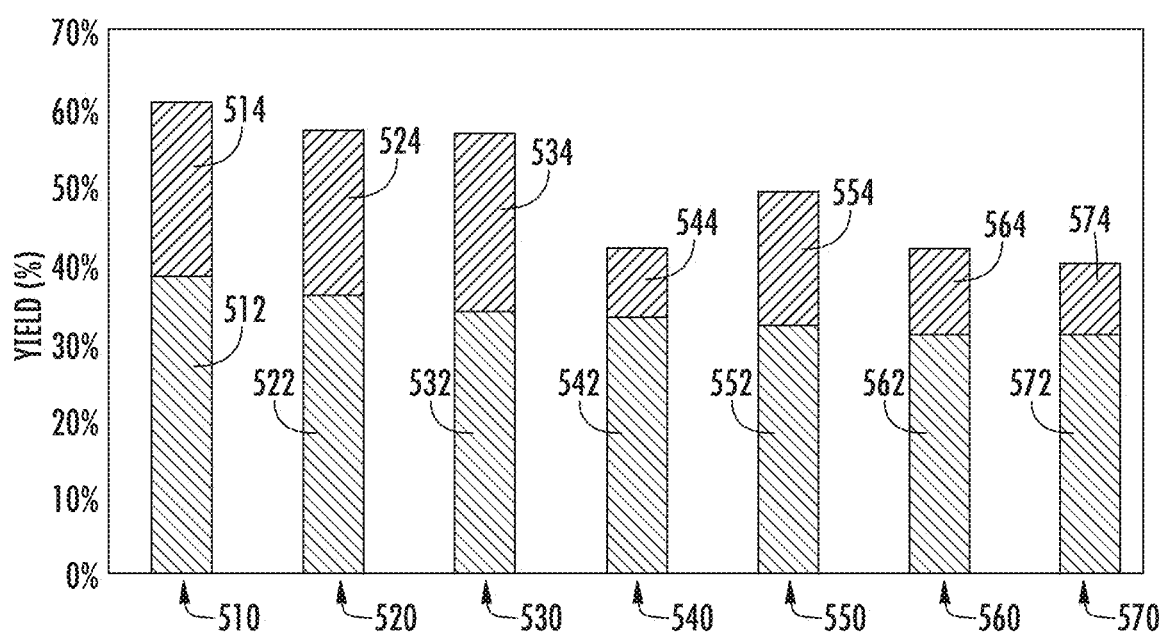
FIG. 5 graphically depicts the propene and ethylene yield (y-axis) obtained from the reaction system of FIG. 4 for converting 2-butene to propene using the composite catalysts of Examples 1-3 (x-axis) the catalyst compositions of Comparative Examples 5-7 (x-axis), in accordance with one or more embodiments of the present disclosure.

The results for absolute propene yield and absolute ethylene yield are provided graphically in FIG. 5. In FIG. 5 reference numbers 512, 522, 532, 542, 552, and 562 refer to the absolute propene yield for each of Comparative Example 5 (510), Example 1 (520), Example 2 (530), Comparative Example 6 (540), Example 3A (550), and Comparative Example 7 (560), respectively. In FIG. 5, reference numbers 514, 524, 534, 544, 554, and 564 refer to the absolute ethylene yield for each of the Examples and Comparative Examples in Table 2.

As shown graphically in FIG. 5, the catalytic performance of the composite catalysts of Examples 1 and 2 were comparable to the performance of Comparative Example 5, for which the catalyst was a mixture of a solid particulate MFI zeolite and a solid particulate metathesis catalyst. Thus, combining the zeolite and the metathesis catalyst into a single composite catalyst, such as the composite catalyst of Examples 1 and 2, did not result in substantially reduced catalytic performance of the composite catalysts compared to the catalytic performance of the physical mixture of catalysts in Comparative Example 5. The time on stream of the reactor system in Example 10 was not of sufficient duration to cause settling of the catalyst mixture of Comparative Example 5. The performance of the composite catalyst of Examples 1 and 2, which included catalytic activity for cracking through incorporation of the MFI zeolite as the preformed catalyst material, was better for both propene yield and ethylene yield compared to the conventional metathesis catalyst of Comparative Example 6 and the metathesis catalyst made by the aerosol method of Comparative Example 7.

Figure 12:
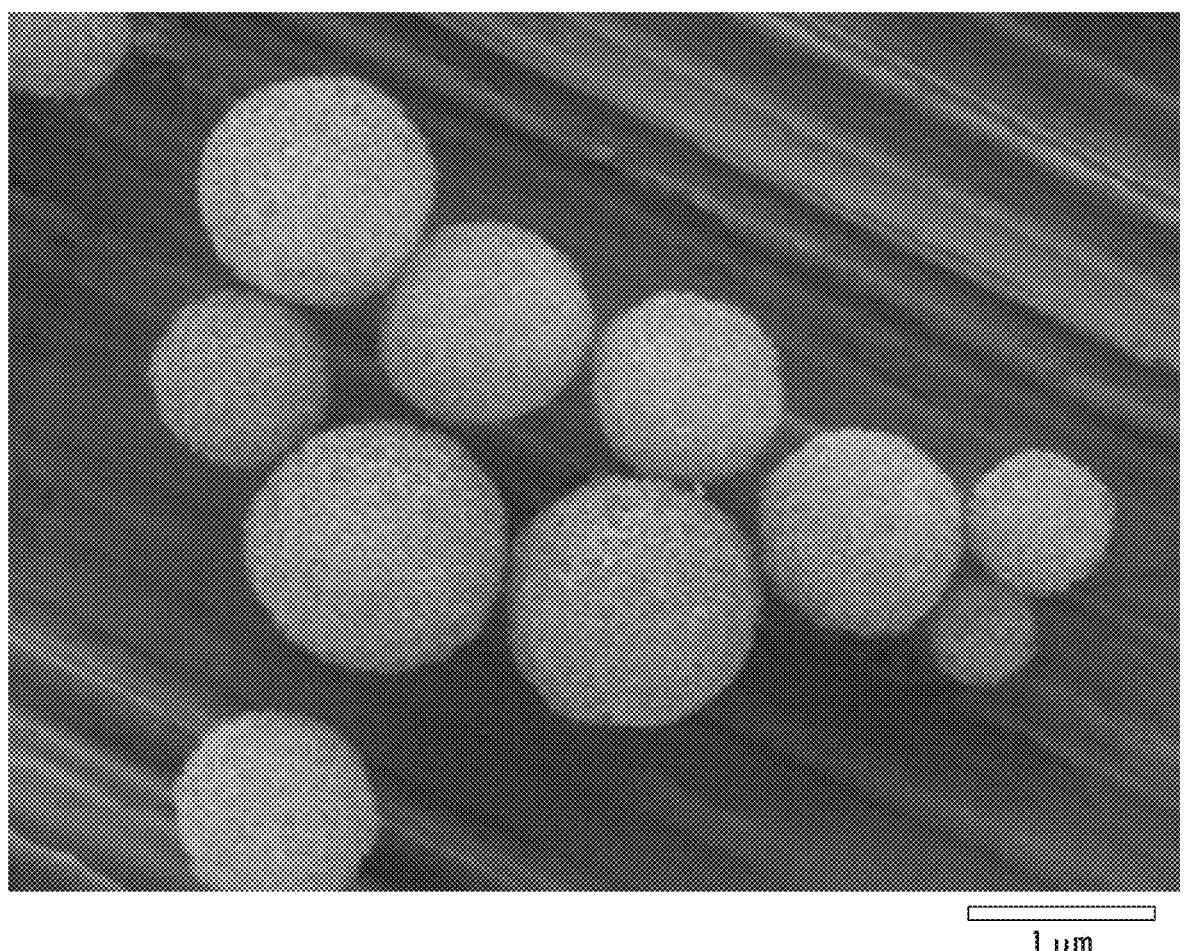
FIG. 12 provides an SEM photograph of a metathesis catalyst without the preformed catalyst material, in accordance with one or more embodiments of the present disclosure.
Figure 13:
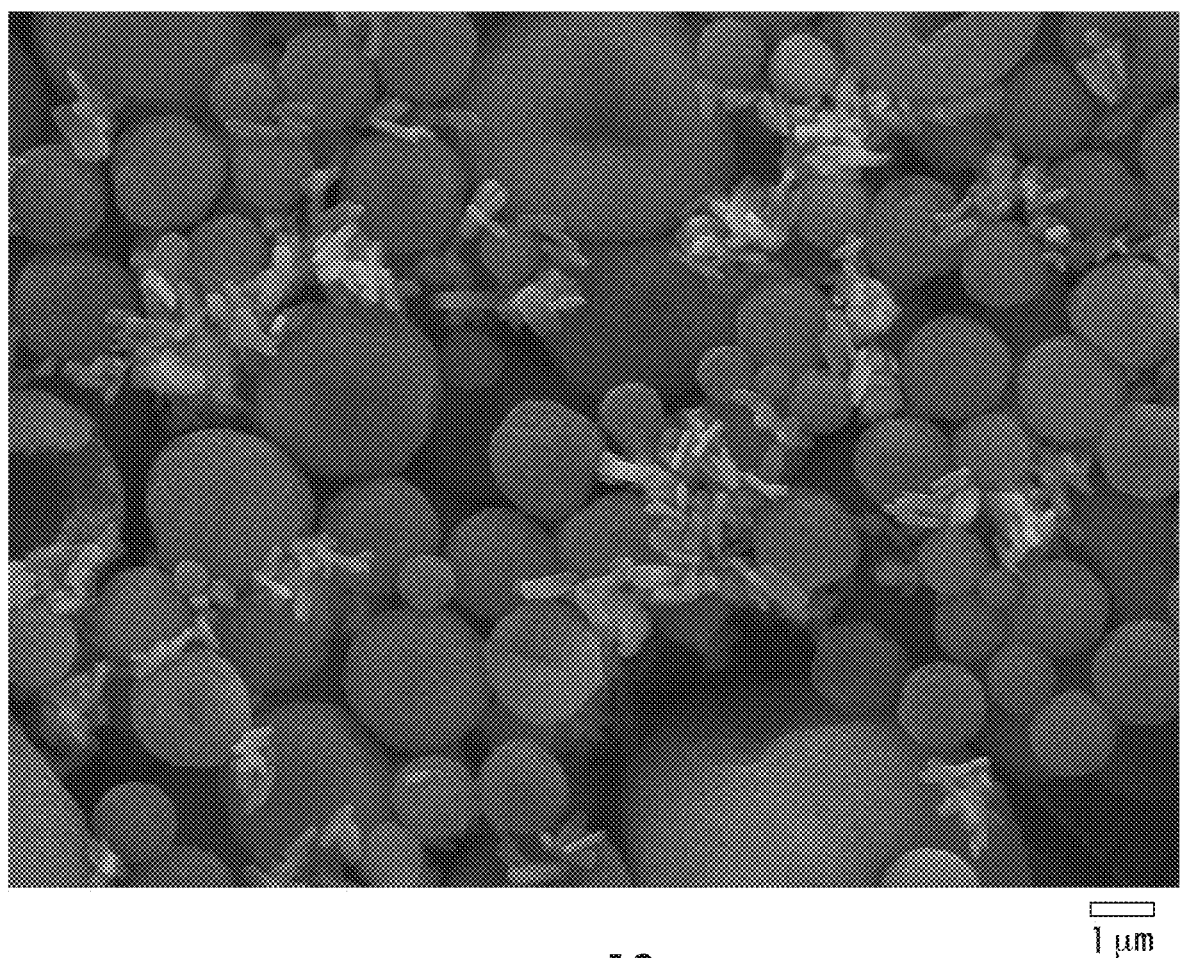
FIG. 13 provides an SEM photograph of a physical mixture of a metathesis catalyst and an MFI zeolite catalyst, in accordance with one or more embodiments of the present disclosure.

Referring to FIG. 6, the combined yield of propene and ethylene is shown for the reaction of 2-butene with the composite catalyst of Example 1 (602), the conventional metathesis catalyst of Comparative Example 6 (604), and a physical catalyst mixture (606) of an MFI zeolite preformed catalyst material with the metathesis catalyst of Comparative including MFI zeolite preformed catalyst materials embedded in the fumed silica catalyst support. As seen in FIG. 11, the smaller elongated zeolite particles are embedded in the fumed silica catalyst support. For comparison, FIG. 12 provides an SEM photograph of a metathesis catalyst. The metathesis catalyst in FIG. 12 does not have zeolite particles embedded within the fumed silica support material. FIG. 13 provides an SEM photograph of a physical mixture of a metathesis catalyst and an MFI zeolite catalyst. As shown in FIG. 13 for the physical catalyst mixture of catalysts, the MFI zeolite material is not embedded at all in the metathesis catalyst, but rather includes a plurality of particles distinct from yet intermingled with the solid particles of the metathesis catalyst.

Partially encasing the zeolite in the tungsten containing silica support material of Example 1 is expected to substantially decrease the activity of the zeolite due to blocking of the catalytically active sites by the tungsten containing silica support and preventing access by reactants to the catalytically active sites on the zeolite. However, as the data graphically shown in FIG. 6 indicates, partially encasing the zeolite in the tungsten containing silica support material of Example 1 did not substantially decrease the catalytic activity of the composite catalyst of Example 1 compared to the simple physical mixture of zeolite and metathesis catalyst of Comparative Example 5, which was unexpected. The zeolite preformed catalyst material in the composite catalyst of Example 1 unexpectedly maintained its catalytic activity despite being at least partially embedded in the tungsten containing silica support material. Without being bound by theory, it is believed that the open porous structure and high surface area of the fumed silica catalyst support material of the composite catalyst of Example 1 allows reactants to efficiently pass through the silica to reach catalytically active sites on the zeolite.

Example 10

Effects of Varying Alumina Content in the Zeolite and Ratio of Zeolite to Metathesis Catalyst on Performance of the Composite Catalysts In Example 10, the effects of varying the alumina content of the zeolite preformed catalyst material and varying the ratio of zeolite preformed catalyst material to the metathesis catalyst portion were evaluated. As referred to in Example 10, the term "metathesis catalyst portion" refers to the catalyst support material and the catalytically active compound. In Example 10, the catalyst support material was fumed silica and the catalytically active compound precursor was ammonium metatungstate hydrate. The fumed silica was AEROSIL® 380 fumed silica marketed by Evonik, and the ammonium metatungstate hydrate was obtained from Strem Chemicals, Inc. The composite catalysts of Example 10 were synthesized according to the aerosol processing method described in Example 1.

Three composite catalysts were made with different combinations of zeolite preformed catalyst material and ratio of zeolite to metathesis catalyst portion of the composite catalyst. For Sample 10A, the zeolite preformed catalyst material was the H-ZSM-5 zeolite P-371 obtained from ACS Material and described previously in Example 3. The zeolite of Sample 10A had a weight ratio of silica to alumina of about 371:1. Sample 10A was made with a weight ratio of zeolite to metathesis portion of the catalyst of 1:1. For Sample 10B, the zeolite preformed catalyst material was MFI-2000, which had a weight ratio of silica to alumina of about 1012:1. Sample 10B was made with a weight ratio of zeolite to metathesis portion of the catalyst of 1:1. For Sample 10C, the zeolite preformed catalyst material was also the H-ZSM-5 zeolite P-371 obtained from ACS Material and used in Sample 10A. Sample 10C was made with a weight ratio of zeolite to metathesis portion of the catalyst of 5:1.

Each of the composite catalysts of Samples 10A, 10B, and 10C were charged individually to the fixed-bed flow reactor system 400 described previously in Example 9. For each composite catalyst individually, a stream containing 2-butene was introduced to the fixed-bed reactor system and the propene yield determined for each of the composite catalysts of Samples 10A, 10B, and 10C.

Figure 7:
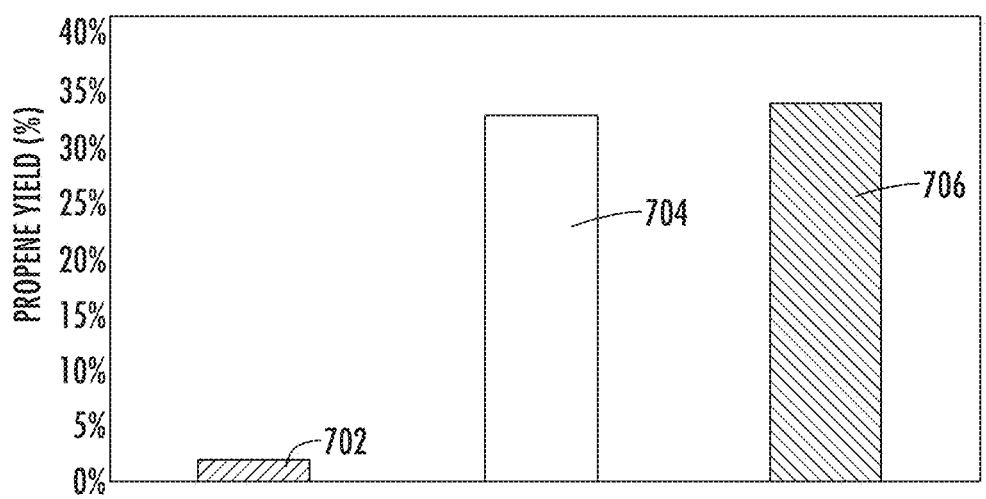
FIG. 7 graphically depicts the propene yield (y-axis) obtained from the reaction system of FIG. 4 for converting 2-butene to propene using composite catalysts of Examples 10 having different weight ratios of zeolite to metathesis catalyst and weight ratios of silica to alumina in the zeolite, in accordance with one or more embodiments of the present disclosure.
Figure 8:
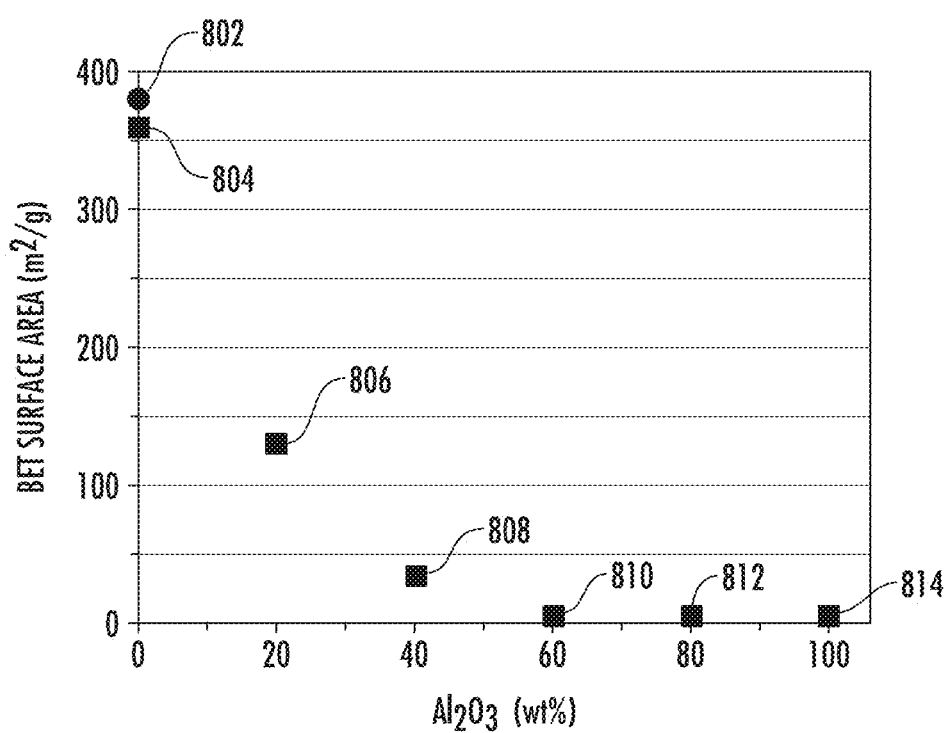
FIG. 8 graphically depicts the BET surface area (y-axis) for catalyst particles having decreasing weight ratios of fumed silica (fumed material) to alumina (non-fumed material) (x-axis), in accordance with one or more embodiments of the present disclosure.
Figure 9:
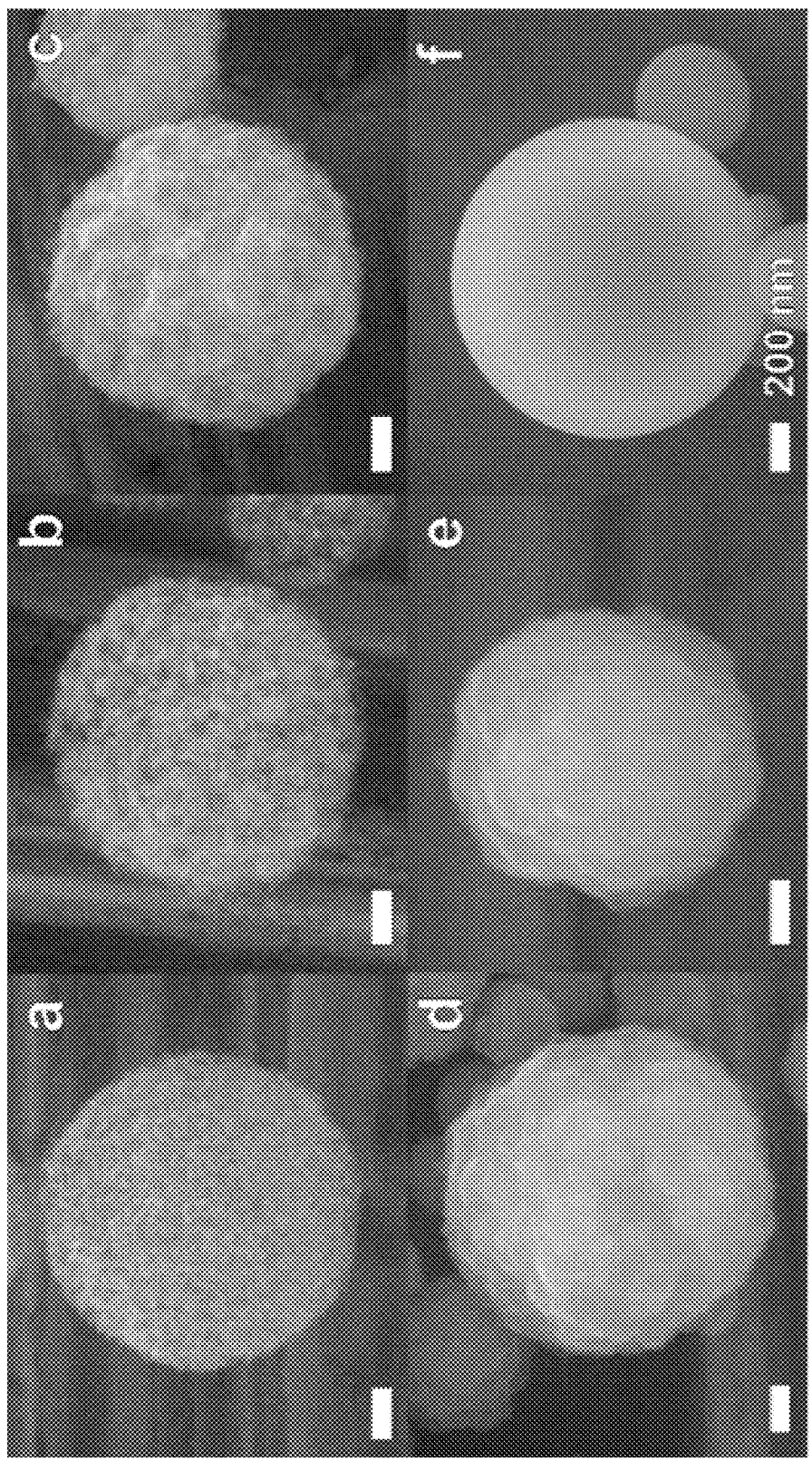
FIG. 9 provides SEM photographs of catalyst particles produced with various weight ratios of fumed silica and non-fumed alumina catalyst support precursors, in accordance with one or more embodiments of the present disclosure.

Referring now to FIG. 7, the propene yield for the composite catalysts of Samples 10A-10C are graphically illustrated. In FIG. 7, Sample 10A is represented by reference number 702, Sample 10B is represented by reference number 704, and Sample 10C is represented by reference number 706. The results in FIG. 7 demonstrate the influence of alumina content of the zeolite on the performance of the composite catalyst. The propene yields for the composite catalysts in FIG. 7 demonstrate that using zeolites with different alumina contents can greatly affect the performance of the composite catalyst. Looking at composite catalysts 702 and 706, which have the same zeolite used for the preformed catalyst material, the activity of the zeolites can be improved by adjusting the amount of zeolite relative to the amount of the tungsten containing silica support material. Changing the weight ratio of the zeolite to the tungsten containing silica support material changes the concentration of alumina per unit volume of the composite catalyst, which may change the performance of the composite catalyst. The controllable activity per volume may enable simultaneous tuning of the other components, such as the metathesis catalyst component, through the addition of more or less of the catalytically active compound as needed. This may be particularly useful for self-metathesis of 2-butene to produce propene because additional reactor volume can be made available for increasing the volume of metathesis catalyst, which may increase the conversion of 2-butene to propene or increasing the space velocity through the reactor system.

It should now be understood that various aspects of the systems and methods of making catalytic materials via aerosol processing are described and such aspects may be utilized in conjunction with various other aspects.

Throughout this disclosure ranges are provided for various processing parameters and characteristics of the metathesis and isomerization catalyst, metathesis catalyst, or isomerization catalyst. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges which may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

What is claimed is:

1. A composite catalyst comprising:
   a catalyst support material that includes at least one of fumed silica, fumed alumina, fumed titania, or combinations of these;
   a preformed catalyst material at least partially secured in the catalyst support where the preformed catalyst material comprises a MFI structured zeolite, a BEA structured zeolite, magnesium oxide, or combinations of these; and
   at least one catalytically active compound supported by the catalyst support material, the preformed catalyst material, or both where the at least one catalytically active compound comprises a metal or metal oxide containing one or more metals selected from the group consisting of magnesium, molybdenum, rhenium, tungsten, manganese, titanium, cerium, and any combination of these; and
   where a catalytic activity of the at least one catalytically active compound is different than a catalytic activity of the preformed catalyst material; wherein the composite catalyst is a spray dried catalyst and
   where a pore volume per unit mass ($cm^3/g$) of the composite catalyst is greater than a pore volume per unit mass of the preformed catalyst material and greater than a pore volume per unit mass of a metathesis catalyst comprising the catalyst support material with the at least one catalytically active compound and without the preformed catalyst material.

2. The composite catalyst of claim 1 where the composite catalyst has an average particle size of from 25 nm to 5 mm.

3. The composite catalyst of claim 1 where the composite catalyst comprises an average surface area of from 100 meters squared per gram to 700 meters squared per gram.

4. The composite catalyst of claim 1 where the catalyst support material forms an open and porous support structure surrounding the preformed catalyst material, the open and porous support structure including an average surface area of from 200 meters squared per gram to 800 meters squared per gram.

5. The composite catalyst of claim 1 where the preformed catalyst material comprises an MFI structured zeolite that has a silica to alumina weight ratio of from 10:1 to 6000:1.

6. The composite catalyst of claim 1 where the composite catalyst has an overall weight ratio of silica to alumina of from 100:1 to 6000:1.

7. The composite catalyst of claim 1 where the preformed catalyst material comprises a ZSM-5 zeolite.

8. The composite catalyst of claim 1 where the at least one catalytically active compound comprises a metathesis catalyst.

9. The composite catalyst of claim 1 where the at least one catalytically active compound comprises a tungsten containing material.

10. The composite catalyst of claim 9 where the tungsten-containing material comprises at least one of tungsten metal, tungsten (IV) oxide, tungsten (VI) oxide, ammonium metatungstate hydrate, tungstic acid, or sodium tungstate.

11. The composite catalyst of claim 1 where the at least one catalytically active compound comprises magnesium oxide.

12. The composite catalyst of claim 1 where the at least one catalytically active compound comprises a tungsten compound and magnesium oxide.

13. The composite catalyst of claim 1 where the preformed catalyst material comprises a MFI structured zeolite that comprises a weight ratio of silica to alumina of from 400:1 to 2000:1, the composite catalyst comprises a weight ratio of the zeolite to the catalyst support material of from 1:1 to 1:19, and the overall silica to alumina weight ratio of the composite catalyst is from 200:1 to 2000:1.

14. The composite catalyst of claim 1 where the at least one catalytically active compound is distributed through the catalyst support material.

15. The composite catalyst of claim 1 where:
the preformed catalyst material is an MFI structured zeolite having a weight ratio of silica to alumina of from 400:1 to 2000:1;
the catalyst support material is fumed silica; and
the catalytically active compound is a tungsten containing material selected from the group consisting of tungsten metal, tungsten (IV) oxide, tungsten (VI) oxide, ammonium metatungstate hydrate, tungstic acid, sodium tungstate, and combinations of these.

16. The composite catalyst of claim 1 made by a method comprising:
generating an aerosolized catalyst precursor mixture by aerosolizing a catalyst precursor mixture comprising the preformed catalyst material, a catalyst support precursor, at least one catalytically active compound precursor, and a diluent, where the preformed catalyst material is a particulate solid and the catalyst support precursor comprises at least one of fumed silica, fumed alumina, fumed titania, or combinations of these; and
drying the aerosolized catalyst precursor mixture to produce a plurality of composite catalyst particles, where drying causes the catalyst support precursor to form an open porous structure of catalyst support material encasing the preformed catalyst material, where the catalytically active compound is distributed throughout the catalyst support material.

17. The composite catalyst of claim 1 where:
the preformed catalyst material is an MFI structured zeolite having a weight ratio of silica to alumina of from 400:1 to 2000:1;
the catalyst support material is fumed silica; and
the catalytically active compound is ammonium metatungstate hydrate.

18. A method of producing a composite catalyst, the method comprising:
generating an aerosolized catalyst precursor mixture by aerosolizing a catalyst precursor mixture comprising a preformed catalyst material, a catalyst support precursor, at least one catalytically active compound precursor, and a diluent, where:
the preformed catalyst material is a particulate solid and comprises a MFI structured zeolite, a BEA structured zeolite, magnesium oxide, or combinations of these;
the catalyst support precursor comprises at least one of fumed silica, fumed alumina, fumed titania, or combinations of these; and
the at least one catalytically active compound precursor comprises a metal or metal oxide containing one or more metals selected from the group consisting of magnesium, molybdenum, rhenium, tungsten, manganese, titanium, cerium, and any combination of these; and
drying the aerosolized catalyst precursor mixture to produce a plurality of composite catalyst particles, where drying causes the catalyst support precursor to form an open porous structure of catalyst support material encasing the preformed catalyst material, where at least one catalytically active compound is distributed throughout the catalyst support material, where the at least one catalytically active compound is supported by the catalyst support, the preformed catalyst material, or both, where the preformed catalyst is at least partially secured in the catalyst support, where a catalytic activity of the at least one catalytically active compound is different than a catalytic activity of the preformed catalyst material, and where a pore volume per unit mass ($cm^3/g$) of the composite catalyst is greater than a pore volume per unit mass of the preformed catalyst material and greater than a pore volume per unit mass of a metathesis catalyst comprising the catalyst support material with the at least one catalytically active compound and without the preformed catalyst material.

19. The method of claim 18 where drying the aerosolized catalyst precursor mixture comprises passing the aerosolized catalyst precursor mixture through a heating zone.

20. The method of claim 19 where a temperature of the heating zone is from 25° C. to 1500° C.

21. The method of claim 18 further comprising introducing a carrier gas to the aerosolized catalyst precursor mixture.

22. The method of claim 18 where generating the aerosolized catalyst precursor mixture comprises introducing the catalyst precursor mixture and a carrier gas to an aerosolizing unit.

23. The method of claim 18 further comprising depositing a supplemental catalytically active compound on surfaces of the catalyst support accessible to vapors and gases.

24. A multi-functional composite catalyst made by the method of claim 18.

25. The multi-functional composite catalyst of claim 24 where the preformed catalyst material comprises a ZSM-5 zeolite.

26. The multi-functional composite catalyst of claim 24 where the catalytically active compound comprises a tungsten containing material.

\* \* \* \* \*